(12) United States Patent
Candelore

(10) Patent No.: US 12,186,438 B2
(45) Date of Patent: Jan. 7, 2025

(54) APPARATUS AND METHOD FOR DISINFECTION OF OBJECT

(71) Applicant: SONY GROUP CORPORATION, Tokyo (JP)

(72) Inventor: Brant Candelore, San Diego, CA (US)

(73) Assignee: SONY GROUP CORPORATION, Tokyo (JP)

( * ) Notice: Subject to any disclaimer, the term of this patent is extended or adjusted under 35 U.S.C. 154(b) by 825 days.

(21) Appl. No.: 17/225,541

(22) Filed: Apr. 8, 2021

(65) Prior Publication Data

US 2022/0323623 A1 Oct. 13, 2022

(51) Int. Cl.
*A61L 2/10* (2006.01)
*A61L 2/26* (2006.01)

(52) U.S. Cl.
CPC .............. *A61L 2/10* (2013.01); *A61L 2/26* (2013.01); *A61L 2202/11* (2013.01); *A61L 2202/20* (2013.01)

(58) Field of Classification Search
CPC .......... A61L 2/10; A61L 2/26; A61L 2202/11; A61L 2202/20
See application file for complete search history.

(56) References Cited

U.S. PATENT DOCUMENTS

| | | | |
|---|---|---|---|
| 9,757,486 | B2 | 9/2017 | Dobrinsky et al. |
| 10,183,085 | B2 | 1/2019 | Dobrinsky |
| 10,543,058 | B2 | 1/2020 | Bauco et al. |
| 2013/0243647 | A1* | 9/2013 | Garner ............... A61L 2/24 250/492.1 |
| 2017/0028088 | A9 | 2/2017 | Maxik et al. |
| 2019/0117811 | A1 | 4/2019 | Barber, III |

(Continued)

FOREIGN PATENT DOCUMENTS

| | | |
|---|---|---|
| CN | 112370541 A | 2/2021 |
| CN | 112604014 A | 4/2021 |
| DE | 102004009687 A1 | 9/2005 |

(Continued)

OTHER PUBLICATIONS

Hayley Peterson, "Amazon Built a Roving Robot Covered in UV light Bulbs that Could Kill the Coronavirus in Warehouses and Whole Foods Stores", Business Insider, May 11, 2020, 04 pages.

*Primary Examiner* — Sean E Conley
(74) *Attorney, Agent, or Firm* — CHIP LAW GROUP

(57) ABSTRACT

An electronic apparatus is provided. The electronic apparatus is coupled with an ultraviolet light source. The electronic apparatus acquires information associated with a first object. The acquired information relates to one of a location of the first object, a distance between the first object and the ultraviolet light source, or an angular orientation of the first object from the ultraviolet light source. The electronic apparatus determines, based on the acquired information, one or more control parameters for the ultraviolet light source to disinfect the first object. The one or more control parameters relate to at least one of an amount of time for emission of the ultraviolet light, a wavelength of an ultraviolet light emitted by the ultraviolet light source, or an inclination of the emitted ultraviolet light. The electronic apparatus controls, based on the determined one or more control parameters, the ultraviolet light source to disinfect the first object.

14 Claims, 8 Drawing Sheets

(56) References Cited

U.S. PATENT DOCUMENTS

2023/0277702 A1\* 9/2023 Wendt ...................... A61L 2/28
                                                         422/24

FOREIGN PATENT DOCUMENTS

| KR | 10-0668938 B1 | 1/2007 |
|---|---|---|
| WO | 2011/033263 A1 | 3/2011 |
| WO | 2018/190566 A1 | 10/2018 |

\* cited by examiner

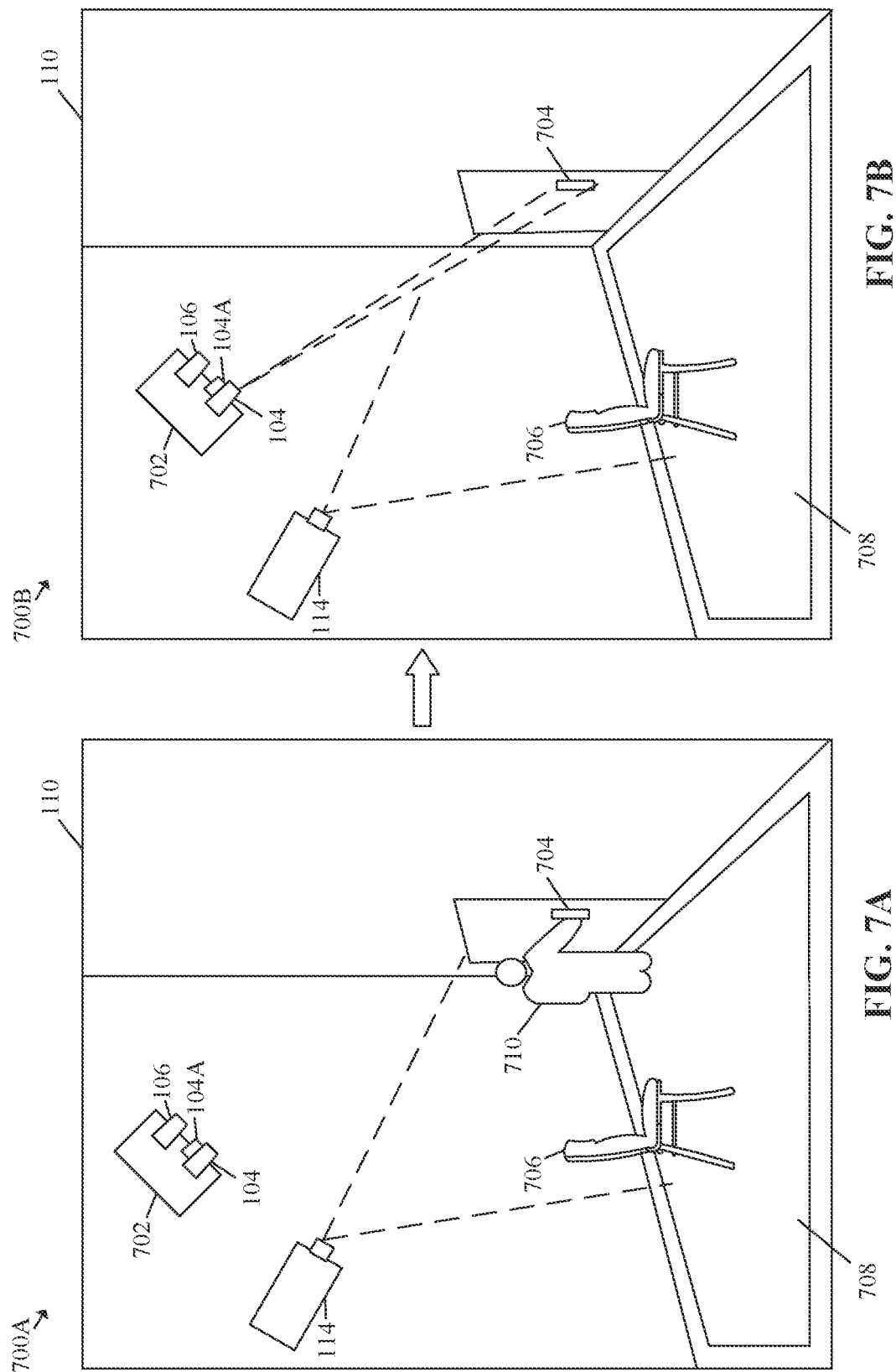

APPARATUS AND METHOD FOR DISINFECTION OF OBJECT

CROSS-REFERENCE TO RELATED APPLICATIONS/INCORPORATION BY REFERENCE

None.

FIELD

Various embodiments of the disclosure relate to disinfection of an object. More specifically, various embodiments of the disclosure relate to an apparatus and method for disinfection of an object.

BACKGROUND

Pathogens (such as viruses) may be transmitted through contact with respiratory droplets of an infected person. An individual may be infected when the individual touches a surface contaminated with the pathogens and then touches his/her face. For example, pathogens may transfer from one individual to another individual based on interaction of the individuals with an exposed surface of an object (such as a door knob, an elevator button, a table top surface, a seat, and so on). In some cases, the contaminated surface may be manually disinfected by application of a disinfection medium (such as a disinfectant fluid spray). However, the effectiveness of the disinfection medium may depend on the frequency (every hour or every two hours) of manual disinfection of the potentially contaminated surface and may not be based on actual usage or contamination of the surface. Even if the surface is frequently disinfected, the effectiveness may further depend on usage of a proper amount of the disinfection medium and coverage of the surface. In some cases, the contaminated surface may be positioned at an inclination, which may conceal a part of the surface from the disinfection medium. Such inclination may prevent the disinfection medium to disinfect all portions of the object. Further, in some cases, frequent use of the disinfection medium (such as disinfectant fluid spray) may not be suitable for all types of objects (such as wooden surfaces, keyboard, or fiber), and may tend to damage aesthetic or structural aspects of the objects.

Further limitations and disadvantages of conventional and traditional approaches will become apparent to one of skill in the art, through comparison of described systems with some aspects of the present disclosure, as set forth in the remainder of the present application and with reference to the drawings.

SUMMARY

An apparatus and method for disinfection of an object is provided substantially as shown in, and/or described in connection with, at least one of the figures, as set forth more completely in the claims.

These and other features and advantages of the present disclosure may be appreciated from a review of the following detailed description of the present disclosure, along with the accompanying figures in which like reference numerals refer to like parts throughout.

BRIEF DESCRIPTION OF THE DRAWINGS

FIGS. 7A and 7B are diagrams that collectively illustrate an exemplary scenario for control of an ultraviolet light source, based on priority of disinfection, in accordance with an embodiment of the disclosure.

DETAILED DESCRIPTION

Figure 1:
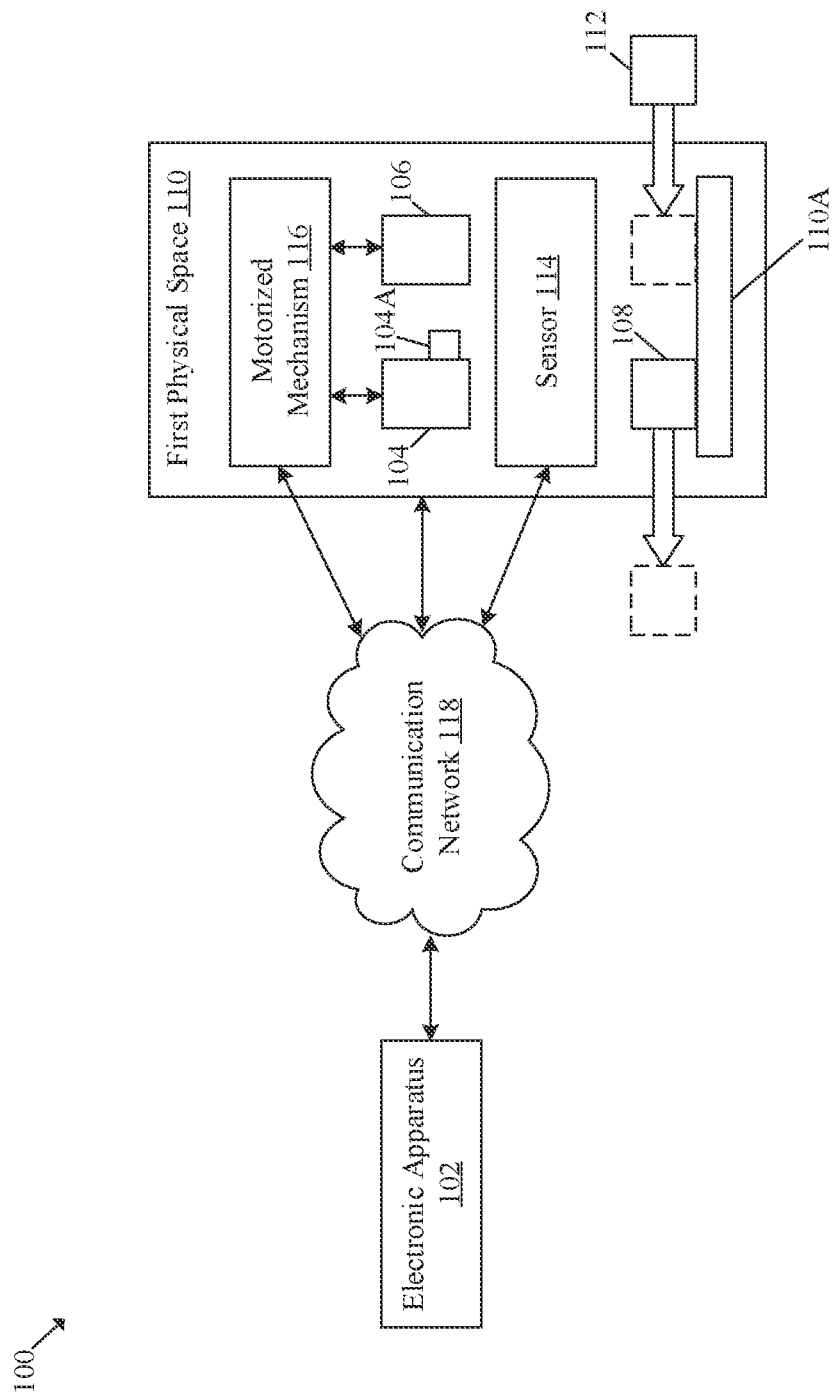
FIG. 1 is a block diagram that illustrates an exemplary network environment of an electronic apparatus to control an ultraviolet light source for disinfection of an object, in accordance with an embodiment of the disclosure.

The following described implementations may be found in a disclosed electronic apparatus and method for disinfection of an object. Exemplary aspects of the disclosure provide an electronic apparatus which may be implemented in a first physical space (such as a room, an elevator, a park, etc.). The electronic apparatus may be communicably coupled with an ultraviolet light source. The electronic apparatus may be configured to acquire information associated with a first object (such as a book, a table, a door knob, a seat, a keypad, a button panel, etc.) located in a first physical space (such as a room, an elevator, a park, etc.). The information may be related to at least one of a location of the first object in the first physical space, a distance between the first object and the ultraviolet light source, or an angular orientation of the first object with respect to the ultraviolet light source. The electronic apparatus may further determine, based on the acquired information, one or more control parameters for the ultraviolet light source to disinfect the first object. The one or more control parameters may be related to at least one of an amount of time (for example, a few seconds to a few minutes) for emission of the ultraviolet light by the ultraviolet light source, a wavelength (for example, UVA, UVB, or UVC) of the emitted ultraviolet light, an intensity of the emitted ultraviolet light, or an inclination of the emitted ultraviolet light. The electronic apparatus may further control, based on the determined one or more control parameters, the ultraviolet light source to disinfect the first object.

For example, the electronic apparatus may control the ultraviolet light source to emit the ultraviolet light of a specific wavelength and a specific intensity for the amount of time. Thus, the electronic apparatus may control the emission of the ultraviolet light for a different amount of time based on the distance between the first object and the ultraviolet light source, to thereby effectively kill or inactivate pathogens on the first object. Further, the electronic apparatus may control the inclination of the emitted ultraviolet light based on the angular orientation of the first object with respect to the ultraviolet light source, to thereby effectively disinfect all portions of the first object. Further, the electronic apparatus may control the emission of the ultraviolet light based on detection of usage of the first object, to thereby timely disinfect the first object post usage and prior to subsequent use of the first object.

In some cases, the first object may be located at a short distance from the ultraviolet light source. In such cases, the ultraviolet light source may disinfect the first object within a short amount of time. The electronic apparatus may determine a short amount of time (such as 90 seconds) for the emission of the ultraviolet light to effectively disinfect the first object. In certain cases, the first object may be located farther away from the ultraviolet light source. In such cases, the electronic apparatus may determine a longer amount of time (such as 120 seconds) for the emission of the ultraviolet light to effectively disinfect the first object. Advantageously, the electronic apparatus may also determine and control the wavelength, or the intensity of the ultraviolet light emitted by the ultraviolet light source, based on the acquired distance between the first object and the ultraviolet light source, for disinfection of the first object.

In some cases, the first object may be positioned at an inclination with respect to the ultraviolet light source in the first physical space, which may conceal a portion of the first object from the emitted ultraviolet light. In such cases, the electronic apparatus may be configured to determine the inclination of the ultraviolet light emitted by the ultraviolet light source, such that the determined inclination may allow the ultraviolet light source to disinfect the concealed portion of the first object. In some cases, there may be a second object (such as a person) that may be detected, as an animate object, in the first physical space. Based on the detection of the second object, the electronic apparatus may be configured to notify the second object about the disinfection of the first object, or may control the ultraviolet light source to switch off, such that, the irradiation from the ultraviolet light source may not damage any part (such as eyes or skin) of the person.

Reference will now be made in detail to specific aspects or features, examples of which are illustrated in the accompanying drawings. Wherever possible, corresponding or similar reference numbers will be used throughout the drawings to refer to the same or corresponding parts.

FIG. 1 is a block diagram that illustrates an exemplary network environment of an electronic apparatus to control an ultraviolet light source for disinfection of an object, in accordance with an embodiment of the disclosure. With reference to FIG. 1, there is shown a network environment 100. In the network environment 100, there is shown an electronic apparatus 102. In the network environment 100, there is further shown an ultraviolet light source 104 and a visible light source 106 within a first physical space 110. The electronic apparatus 102 may be configured to control the ultraviolet light source 104 to disinfect a first object 108 that may be disposed in a first physical space 110. In an embodiment, the ultraviolet light source 104 may include a lighting device 104A that may be configured to be illuminate the first object 108 based on the detection of a second object 112. In the network environment 100, there is further shown a sensor 114 configured to detect at least one of the first object or the second object. In the network environment 100, there is further shown a motorized mechanism 116 configured to control at least one of the ultraviolet light source 104 or the visible light source 106. In the network environment 100, there is further shown a communication network 118. The electronic apparatus 102 may be communicably coupled with the ultraviolet light source 104, the visible light source 106, the sensor 114, and the motorized mechanism 116 via the communication network 118.

The network environment 100 may be an exemplary representation of components (such as the ultraviolet light source 104, the visible light source 106, the first physical space 110, the sensor 114, and the motorized mechanism 116), which may be associated with the electronic apparatus 102. In an embodiment, the network environment 100 may include fewer or more elements than those illustrated and described in the present disclosure. For example, the network environment 100 may not include the visible light source 106, without deviating from the scope of the disclosure.

The electronic apparatus 102 may include suitable logic, circuitry, and interfaces that may be configured to acquire information associated with the first object 108 located in the first physical space 110. The electronic apparatus 102 may further determine, based on the acquired information, one or more control parameters for the ultraviolet light source 104 to disinfect the first object 108. The electronic apparatus 102 may further configured to control, based on the determined one or more control parameters, the ultraviolet light source 104 to disinfect the first object 108. Details of the electronic apparatus 102 for control of the ultraviolet light source 104 are further described, for example, in FIGS. 3A-3C, 4A, 4B, 5A-5C, 6A-6C, 7A, and 7B. The electronic apparatus 102 may include an application (downloadable from a cloud server) that may include a user interface to manage the one or more control parameters for the ultraviolet light source 104 and control the ultraviolet light source 104. Examples of the electronic apparatus 102 may include, but are not limited to, a computing device, a mainframe machine, a computer workstation, a mobile phone, a smart phone, a tablet computing device, a personal computer, a smart audio device, a server, and/or a consumer electronic (CE) device with communication and information processing capability.

In an embodiment, the electronic apparatus 102 may be implemented as a mobile device that may be communicably coupled with at least one of the ultraviolet light source 104, the visible light source 106, the sensor 114, and the motorized mechanism 116. The mobile device may include suitable logic, circuitry, interfaces and/or code that may be configured to present audio data, video data, and a user interface to receive the information (such as the location, the distance, or the angular orientation) associated with the first object 108 located in the first physical space 110, and control the ultraviolet light source 104, based on the one or more control parameters (such as the amount of time, the wavelength, or the inclination of the ultraviolet light). Examples of the mobile device may include, but are not limited to, a computing device, a smartphone, a cellular phone, a mobile phone, and other portable devices.

In another embodiment, the electronic apparatus 102 may be implemented as a server. In an embodiment, the server may be a cloud server, which may be utilized to execute various operations through web applications, cloud applications, HTTP requests, repository operations, file transfer, and the like. Examples of the server may include, but are not limited to, an event server, a database server, a file server, a web server, a media server, a content server, an application server, a mainframe server, or a combination thereof. In one or more embodiments, the server may be implemented as a plurality of distributed cloud-based resources to control the ultraviolet light source 104.

Figure 3A:
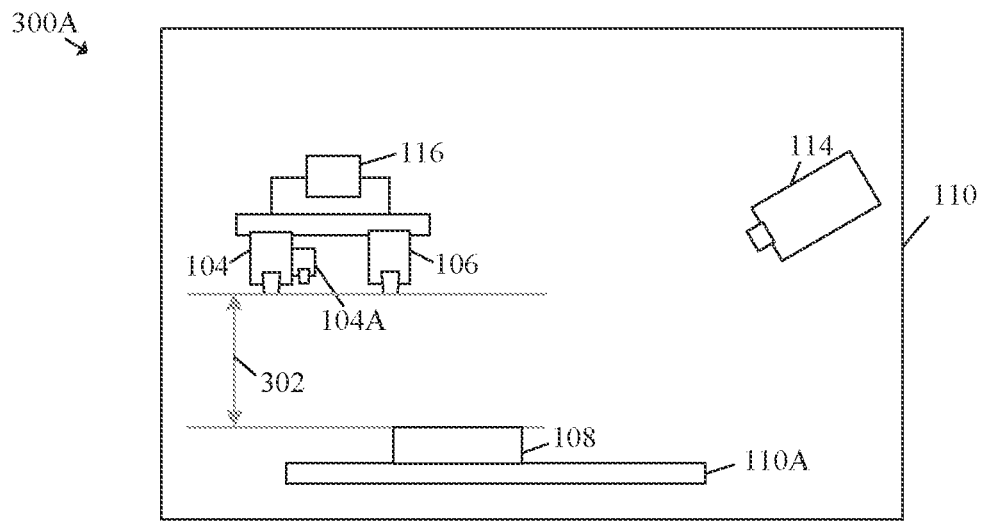
FIGS. 3A-3C are diagrams that collectively illustrate an exemplary scenario for control of an ultraviolet light source, based on a distance between an ultraviolet light source and an object, in accordance with an embodiment of the disclosure.
Figure 3B:
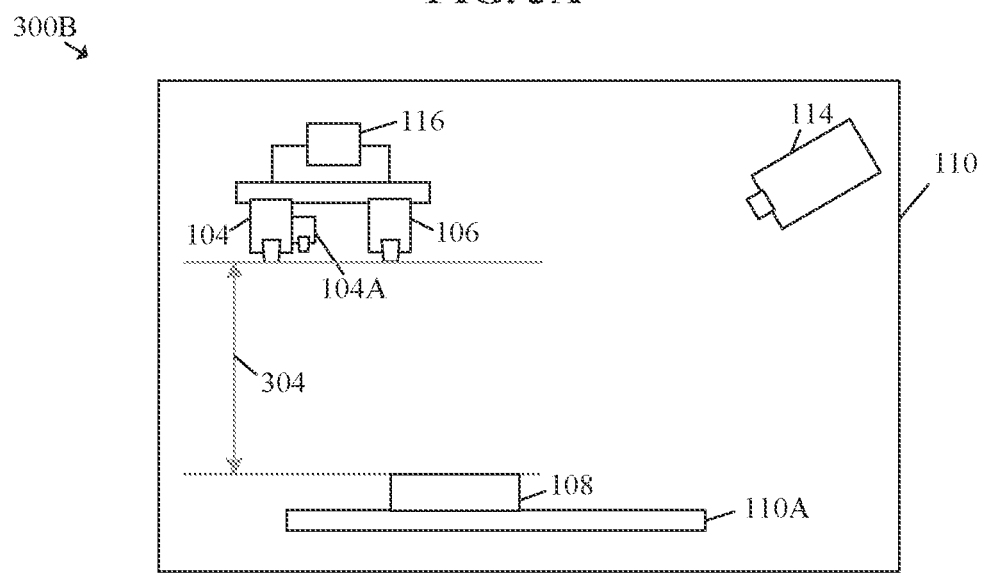
Figure 3C:
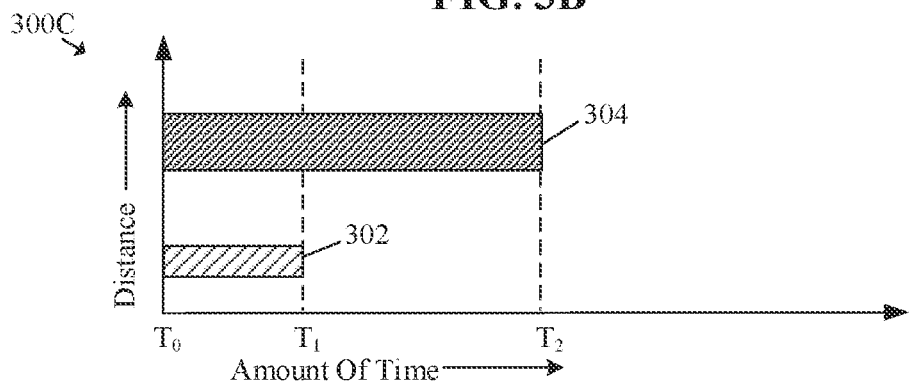

The ultraviolet light source 104 may include suitable logic, circuitry, and interfaces that may be configured to emit the ultraviolet light to disinfect the first object 108. In an embodiment, the ultraviolet light source 104 may comprise a transceiver (such as a Wireless Fidelity (Wi-Fi) transceiver or a Bluetooth™ transceiver) for reception of control signals (such as ON or OFF signals) from the electronic apparatus 102 via the communication network 118. In another embodiment, the ultraviolet light source 104 may comprise a transceiver (such as radio frequency (RF) transceiver or a Bluetooth™ transceiver) for reception of control signals (such as ON or OFF signals, or signals to switch between the ultraviolet light and visible light of the lighting device 104A) from a remote control operable by a user. For example, in case the first object 108 is positioned at a distance (as shown in FIGS. 3A-3C) from the ultraviolet light source 104, the electronic apparatus 102 may control the ultraviolet light source 104 to emit the ultraviolet light on the first object 108, based on the distance from the ultraviolet light source 104. In another example, the electronic apparatus 102 may further control the ultraviolet light source 104 to modify the wavelength (for example, in the range between 100 nm-400 nm) of the emitted ultraviolet light, based on at least one of the distance of the first object 108 from the ultraviolet light source 104, or the location of the first object 108 in the first physical space 110. Examples of the wavelength bands of the emitted ultraviolet light may include, but are not limited to, a UVA Band (for example, in the range between 315-400 nm), a UVB Band (for example, in the range between 280-315 nm), or a UVC Band (for example, in the range between 100-280 nm). Examples of the ultraviolet light source 104 may include, but are not limited to, a black light lamp, a short-wave UV lamp, an incandescent lamp, a gas-discharge lamp (such as a mercury-vapor lamp), an ultraviolet LED lamp, an ultraviolet laser, or a tunable vacuum ultraviolet. In an embodiment, the ultraviolet light source 104 may further include a lighting device 104A that may be configured to emit visible light to notify the second object 112 (such as a person) in the first physical space 110.

In an embodiment, the ultraviolet light source 104 may comprise one or more reflectors for control of one or more parameters (such as intensity, focus, directivity, or emission angle) of the emitted ultraviolet light. In an embodiment, the ultraviolet light source 104 may comprise two or more UV lamps configured to emit ultraviolet light of the same wavelength or different wavelength ranges (such as UVA, UVB, and UVC bands). The electronic apparatus 102 may further control the ultraviolet light source 104 to selectively activate a single UV lamp of the two or more UV lamps to emit the ultraviolet light of a specific wavelength range. In another embodiment, the electronic apparatus 102 may further control the ultraviolet light source 104 to concurrently activate the two or more UV lamps to increase the power or the intensity of the emitted ultraviolet light. In an embodiment, the ultraviolet light source 104 may comprise a three-way switch to switch between ultraviolet light ON, ultraviolet light OFF/visible light ON, and ultraviolet light OFF/visible light OFF.

The lighting device 104A may include suitable logic, circuitry, and interfaces that may be configured to emit visible light to notify the second object 112 about the disinfection of the first object 108. The lighting device 104A may be a combination of software and hardware that may be configured to provide a notification to the second object 112 (for example, one or more users). In an embodiment, the lighting device 104A may comprise a transceiver (such as a Wireless Fidelity (Wi-Fi) transceiver or a Bluetooth™ transceiver) for reception of control signals (such as ON or OFF signals) from the electronic apparatus 102 via the communication network 118. In another embodiment, the lighting device 104A may comprise a transceiver (such as radio frequency (RF) transceiver or a Bluetooth™ transceiver) for reception of control signals (such as ON or OFF signals, or signals to switch between the visible light and the ultraviolet light of the ultraviolet light source 104) from a remote control operable by a user. In an example, based on the received control signals, the lighting device 104A may emit a pulsed illumination to notify the second object 112 about the disinfection of the first object 108. In another example, the lighting device 104A may emit a continuous illumination to notify the second object 112. In another example, the lighting device 104A may project one more characters or symbols (such as a UV radiation warning sign) on to the first object 108 to notify the second object 112. In some embodiments, the notification by the lighting device 104A may be accompanied by another form of notification (such as an audio-based notification, or a vibration-based notification, and the like) to notify the second object 112). In an embodiment, the electronic apparatus 102 may control the lighting device 104A to notify the second object 112, based on the detection of the second object 112 in the first physical space. Examples of the lighting device 104A may include, but are not limited to, an incandescent lighting, a fluorescent lighting, a tungsten-halogen lighting, a Light Emitting Diode (LED) lighting, a High-Intensity Discharge (HID) lighting, or a projection system. Details of the lighting device 104A are further described, for example, in FIGS. 5A-5C.

The visible light source 106 may include suitable logic, circuitry, and interfaces that may be configured to illuminate the first object 108. In an embodiment, the visible light source 106 may comprise a transceiver (such as a Wireless Fidelity (Wi-Fi) transceiver or a Bluetooth™ transceiver) for reception of control signals (such as ON or OFF signals) from the electronic apparatus 102 via the communication network 118. In an example, based on detection of the second object 112, the electronic apparatus 102 may control the visible light source 106 to illuminate the first object 108. In another example, upon completion of the notification (such as the pulsed illumination) from the lighting device 104A, the electronic apparatus 102 may control the visible light source 106 to illuminate the first object 108. In another example, the electronic apparatus 102 may control the ultraviolet light source to switch off based on the detection of the second object 112, and may further control the lighting device 104A to illuminate for a preset time period. The electronic apparatus 102 may then control the visible light source 106 to illuminate the first object 108, based on completion of the first period. Examples of the visible light source 106 may include, but are not limited to, an incandescent lighting, a fluorescent lighting, a tungsten-halogen lighting, a Light Emitting Diode (LED) lighting, or a High-Intensity Discharge (HID) lighting. Details of the visible light source 106 are further described, for example, in FIGS. 5A-5C, and FIGS. 6A-6C.

The first object 108 may be a tangible object that may be disposed in the first physical space 110. In an embodiment, the first object 108 may be displaced from one location to another location in the first physical space 110, as described in FIGS. 6A-6C. In another embodiment, the first object 108 may be displaced from one location to another location by the second object 112 (such as a user). In another embodiment, the electronic apparatus 102 may determine that the second object 112 has come into contact with the first object 108. In such cases, the electronic apparatus 102 may be configured to disinfect the first object 108 to avoid transmission of pathogens from the first object 108. In an embodiment, the first object 108 may include an inanimate object or a non-living entity. Examples of the first object 108 may include, but are not limited to, a chair, a table, a package, an article attached/embedded with a radio-frequency identification (RFID) tag, a pen, a device, an elevator button panel, a door knob, a door handle, a keypad, a book, a mat, a carpet, and other inanimate objects that may be disposed in the first physical space 110. In another embodiment, the first object 108 may also include a consumable (such as water, medicines, or a food item).

The first physical space 110 may be a three-dimensional space that may be defined by one or more boundaries. For example, the boundaries may include walls and/or a roof of a room that houses the first object 108. In another example, the boundaries of the first physical space 110 may be defined by the emission range of the ultraviolet light source 104 or the visible light source 106. Examples of the components that may be disposed in the first physical space 110 may include, but are not limited to, the electronic apparatus 102, the ultraviolet light source 104, the visible light source 106, the first object 108, the second object 112, the sensor 114, and the motorized mechanism 116. In an embodiment, based on a type of the first physical space 110, the electronic apparatus 102 may control the ultraviolet light source 104. The first physical space 110 may be an indoor space or an outdoor space. For example, in case the first physical space 110 is an outdoor space (such as a public park), the electronic apparatus 102 may control the ultraviolet light source 104 to emit the ultraviolet light at a first intensity to disinfect the first object 108. In another example, in case the first physical space 110 is an indoor space (such as a hospital lobby), the electronic apparatus 102 may control the ultraviolet light source 104 to emit the ultraviolet light at a second intensity to disinfect the first object 108. The second intensity may be different from the first intensity of the ultraviolet light. The first physical space 110 may include the base 110A (such as a floor, a table top, a countertop, a tray, a seating surface, a bed, etc.). The first object 108 may be disposed on the base 110A or attached to the base 110A. Examples of each of the first physical space 110 may include, but are not limited to, a living room, an office cabin, a conference room, a meeting room, an auditorium, a warehouse, a classroom, a lobby, an elevator cabin, an escalator, a vestibule, an entertainment park, a restaurant, a sports ground, a movie/music theater, a mall, a clubhouse, an event area, or any enclosure. In an embodiment, the first physical space 110 may also have an access (such as a door or a gate) for the second object 112 to enter the first physical space 110.

The second object 112 may be an animate object or a living entity that may enter and exit the first physical space 110. In an embodiment, the second object 112 may displace the first object 108 from one location to another location in the first physical space 110, as described in FIGS. 6A-6C. In another embodiment, the second object 112 may come in contact with the first object 108, and may be either the source of pathogens deposited on the first object 108 or recipient of pathogens from the first object 108. In such cases, the electronic apparatus 102 may be configured to disinfect the first object 108 to avoid transmission of pathogens from the first object 108. Examples of the second object 112 may include, but are not limited to, a human, an animal, a bird, and other living entities that may enter the first physical space 110. In another embodiment, the second object 112 may include any non-living entities. Examples of the second object 112 may include, but are not limited to, a robot, a drone, a vehicle, a cart, a trolley, and other non-living entities that may enter the first physical space 110. When the second object 112 enters the first physical space 110, the electronic apparatus 102 may control the sensor 114 to acquire the information associated with the second object 112 in the first physical space 110. Details of the second object 112 are further described, for example, in FIGS. 5A-5C.

The sensor 114 may include suitable logic, circuitry, and interfaces that may be configured to capture an image or a plurality of images of objects (for example, the ultraviolet light source 104, the visible light source 106, the first object 108, or the second object 112) in the first physical space 110. Based on the captured images, the sensor 114 may be further configured to acquire the information associated with at least one of the ultraviolet light source 104, the visible light source 106, the first object 108, or the second object 112 in the first physical space 110. For example, the acquired information associated with the first object 108 may include information about a location of the first object 108 or the second object 112 within the first physical space 110, a movement of the first object 108, a distance between the first object 108 and the ultraviolet light source 104, or a refractive index of the first object 108. In an embodiment, based on the acquired information of the first object 108, the electronic apparatus 102 may be further configured to control the one or more control parameters for the ultraviolet light source 104 to disinfect the first object 108. In another embodiment, the sensor 114 may be an infrared sensor that may detect presence of the second object 112 in the physical space.

In another embodiment, the electronic apparatus 102 may be configured to control at least one sensor (such as the sensor 114 or a plurality of sensors) to detect the first object 108 in the first physical space 110. The electronic apparatus 102 may further determine the information associated with the second object 112 based on the detected first object 108 within the first physical space 110. Examples of the sensor 114 may include, but are not limited to, an image sensor, a wide-angle camera, an action camera, a closed-circuit television (CCTV) camera, a camcorder, a digital camera, camera phones, a time-of-flight camera (ToF camera), a night-vision camera, or other image capture devices.

In an embodiment, the sensor 114 may be implemented as a 360-degree camera to detect interactions (such as the tactile contact) between the first object 108 and the second object 112 in X-axis, Y-axis, and Z-axis directions. The 360-degree camera may capture a 360-degree view of the surroundings of the first physical space 110. In accordance with an embodiment, the 360-degree camera may further include a plurality of image sensors that may be configured to capture the 360-degree view. Each image sensor of the plurality image sensors may be configured to capture a portion of the 360-degree view of the surroundings of the first object 108 and/or the second object 112. In accordance with an embodiment, the 360-degree camera may be configured to stitch each captured portion of the plurality image sensors to generate the 360-degree view of the surroundings of the first object 108 and/or the second object 112. In accordance with an embodiment, the 360-degree camera may be installed on at least one of the first object 108, the second object 112, or any position within the first physical space 110. Examples of the 360-degree camera may include, but are not limited to, an omnidirectional camera, a panoramic camera, an action camera, a wide-angle camera, a closed-circuit television (CCTV) camera, and/or other image capturing or devices with 360-degree view capturing capability.

Figure 4A:
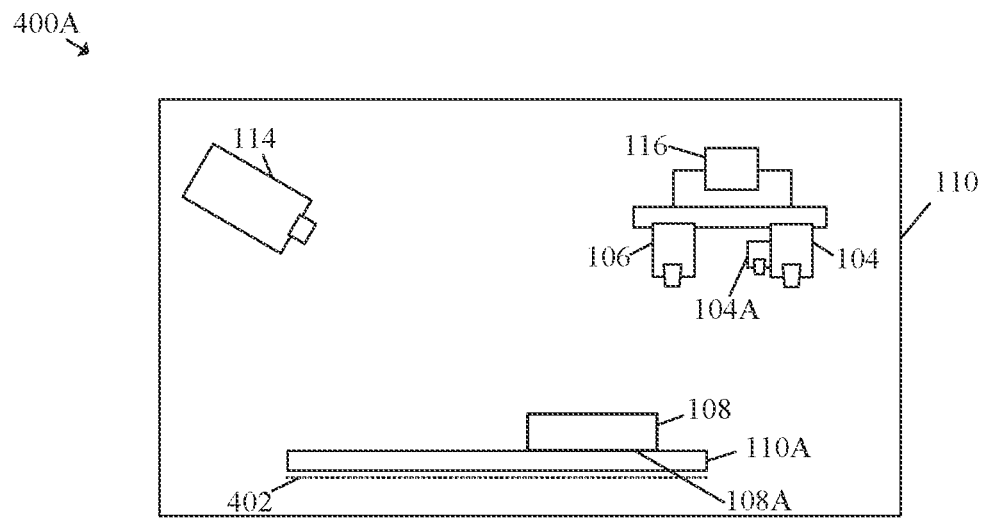
FIGS. 4A and 4B are diagrams that collectively illustrate an exemplary scenario for control of an ultraviolet light source, based on an angular orientation of an object from an ultraviolet light source, in accordance with an embodiment of the disclosure.
Figure 4B:
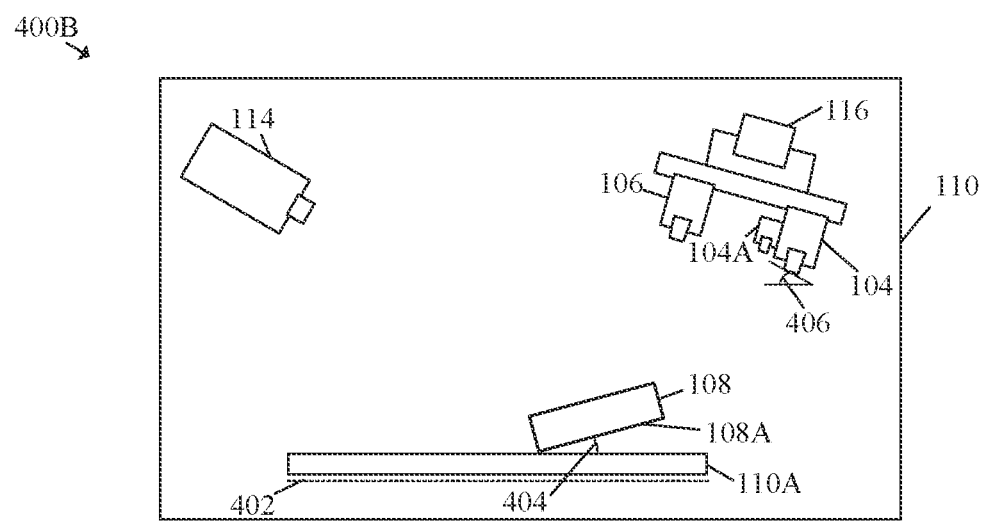

In another embodiment, the sensor 114 may be implemented as a location sensor. The location sensor may include suitable logic, circuitry, and/or interfaces that may be configured to determine a current geo-location of at least one of: the first object 108, the second object 112, or the first physical space 110. Examples of the location sensor may include, but are not limited to, a Global Positioning Sensor (GPS), Global Navigation Satellite System (GLONASS), or other regional navigation systems or sensors. In an embodiment, the sensor 114 may detect an angular orientation (as shown in FIGS. 4A and 4B) of first object 108, the electronic apparatus 102 may control the motorized mechanism 116 associated with the ultraviolet light source 104, to control an inclination of the ultraviolet light source 104, based on the acquired information as the angular orientation of the first object 108 in the first physical space 110. Other examples of the sensor 114 may include, but are not limited to, an infrared (IR) sensor that may detect IR radiation from the first object 108 or the second object 112, an audio sensor that may detect sounds generated by the first object 108 or the second object 112, a light detection and ranging (LiDAR) sensor that may detect a distance between the sensor 114 and the first object 108, a radio detection and ranging (RADAR) sensor that may detect a movement of the first object 108, or a radio-frequency identification (RFID) reader that may read data from the RFID tag attached to or embedded in the first object 108.

The motorized mechanism 116 may include suitable logic, circuitry, and interfaces that may be configured to control a movement of the ultraviolet light source 104. For example, the movement may include, but is not limited to, a rotation, a translational motion, or an inclination of the ultraviolet light source 104. In an embodiment, the electronic apparatus 102 may control the motorized mechanism 116 to control the inclination of the ultraviolet light source 104, based on the acquired information (such as the angular orientation of the first object 108 in the first physical space 110). In another embodiment, the electronic apparatus 102 may control the motorized mechanism 116 to control the rotation of the ultraviolet light source 104, based on the acquired information (such as the angular orientation of the first object 108 in the first physical space 110). In yet another embodiment, the electronic apparatus 102 may control the motorized mechanism 116 to control the translational motion of the ultraviolet light source 104, based on the acquired information (such as the location of the first object 108 in the first physical space 110). The motorized mechanism 116 may include at least one motor that may be configured to control the movement of the ultraviolet light source 104. In an example, the motorized mechanism 116 may include at least one motor and a rack and pinion arrangement to control the translational motion of the ultraviolet light source 104. Examples of the motorized mechanism 116 may include, but are not limited to, a servo motor, a linear motor, a stepper motor or other geared motors. Details of the motorized mechanism 116 are further described, for example, in FIGS. 4A and 4B.

The communication network 118 may include a communication medium through which the electronic apparatus 102, the ultraviolet light source 104, the visible light source 106, the first object 108, the second object 112, the sensor 114, and the motorized mechanism 116, may communicate with each other. The communication network 118 may be one of a wired connection or a wireless connection. Examples of the communication network 118 may include, but are not limited to, the Internet, a cloud network, a Wireless Fidelity (Wi-Fi) network, a Personal Area Network (PAN), a Local Area Network (LAN), or a Metropolitan Area Network (MAN). Various devices in the network environment 100 may be configured to connect to the communication network 118 in accordance with various wired and wireless communication protocols. Examples of such wired and wireless communication protocols may include, but are not limited to, at least one of a Transmission Control Protocol and Internet Protocol (TCP/IP), User Datagram Protocol (UDP), Hypertext Transfer Protocol (HTTP), File Transfer Protocol (FTP), Zig Bee, EDGE, IEEE 802.11, light fidelity (Li-Fi), 802.16, IEEE 802.11s, IEEE 802.11g, multi-hop communication, wireless access point (AP), device to device communication, cellular communication protocols, and Bluetooth (BT) communication protocols. In an embodiment, based on the communication network 118, the electronic apparatus 102 may acquire information associated with the first object 108 located in the first physical space 110. Based on the acquired information and the determined one or more control parameters, the electronic apparatus 102 may control, via the communication network 118, the ultraviolet light source 104 to disinfect the first object.

In operation, the electronic apparatus 102 may be configured to acquire information associated with the first object 108 located in the first physical space 110. For example, the sensor 114 may acquire information associated with the first object 108 located in the first physical space 110. The acquired information may be related to at least one of the location of the first object 108 in the first physical space 110, the distance of the first object 108 from the ultraviolet light source 104 (as described in FIGS. 3A-3C), or the angular orientation of the first object 108 with respect to the ultraviolet light source 104, or with respect to the base 110A of the first physical space 110 (as described in FIGS. 4A and 4B). The electronic apparatus 102 may be further configured to determine, based on the acquired information, one or more control parameters for the ultraviolet light source 104 to disinfect the first object 108. For example, the one or more control parameters may relate to at least one of the amount of time for emission of an ultraviolet light from the ultraviolet light source 104 (as described in FIG. 3C), the wavelength of the emitted ultraviolet light (as described in FIGS. 3A-3C), the intensity of the emitted ultraviolet light (as described in FIGS. 3A-3C), or the inclination of the emitted ultraviolet light (as described in FIGS. 4A and 4B). The electronic apparatus 102 may be further configured to control, based on the determined one or more control parameters, the ultraviolet light source 104 for a first period to disinfect the first object 108.

The electronic apparatus 102 may control the ultraviolet light source 104 to emit the ultraviolet light of a specific wavelength (for example UVC) for the amount of time (such as 90 seconds or 120 seconds) to disinfect the first object 108. Thus, the electronic apparatus 102 may control the emission of the ultraviolet light for a different amount of time based on the distance between the first object 108 and the ultraviolet light source 104, to thereby effectively kill or inactivate pathogens on the first object 108. Further, the electronic apparatus 102 may control the inclination of the emitted ultraviolet light based on the angular orientation of the first object 108 with respect to the ultraviolet light source 104, to thereby effectively disinfect all portions of the first object 108. Further, the electronic apparatus 102 may control the emission of the ultraviolet light based on detection of usage (such as contact with the second object 112) of the first object 108 by the sensor 114, to thereby timely disinfect the first object 108 post usage and prior to subsequent use of the first object 108. Details of the control the emission of the ultraviolet light based on detection of usage are described, for example, in 7A and 7B.

In an embodiment, the electronic apparatus 102 may further control the ultraviolet light source 104 to switch off based on the detection of the second object 112 via the sensor 114. Based on the detected second object 112, the electronic apparatus 102 may further control the lighting device 104A to illuminate the first object 108 for a specific time period (such as 10 seconds). Based on completion of the time period, the electronic apparatus 102 may further control the visible light source 106 to illuminate the first object 108. Thus, the electronic apparatus 102 may ensure safety of the second object 112 (such as the user) from exposure to harmful ultraviolet radiation. Details of the control of the ultraviolet light source 104 and the visible light source 106 are further described, for example, in 5A-5C.

In an embodiment, the electronic apparatus 102 may further control the ultraviolet light source 104 to switch off based on the detection of an animate object as the first object 108. The electronic apparatus 102 may further control the visible light source 106 to illuminate the first object 108 detected as the animate object in the first physical space 110. In another embodiment, the electronic apparatus 102 may detect a second object 112, as an animate object, in the first physical space 110. The electronic apparatus 102 may notify the second object 112 about the disinfection of the first object 108. The notification may comprise at least one of a pulsed illumination of the lighting device 104A associated with the ultraviolet light source 104, or an audible alert for the second object 112. Thus, the electronic apparatus 102 may ensure safety of the second object 112 (such as the user) by notification of harmful ultraviolet radiation. Details of the notification are further described, for example, in 5A-5C.

In an embodiment, the acquired information may indicate a set of objects including the first object in the first physical space 110. The electronic apparatus 102 may determine a level of priority for disinfection of each object of the set of objects based on the determined type of each object in the first physical space 110. The electronic apparatus 102 may control the ultraviolet light source to disinfect each object of the set of objects based on the determined level of priority of disinfection for each object in the first physical space 110. Details of the control of the ultraviolet light source based on the determined level of priority are further described, for example, in 7A and 7B.

In an embodiment, the ultraviolet light source 104 is a first bulb and the visible light source 106 is a second bulb. The first bulb and the second bulb are held by a dual fixture. In another embodiment, the ultraviolet light source and the visible light source are disposed in a single bulb.

Figure 2:
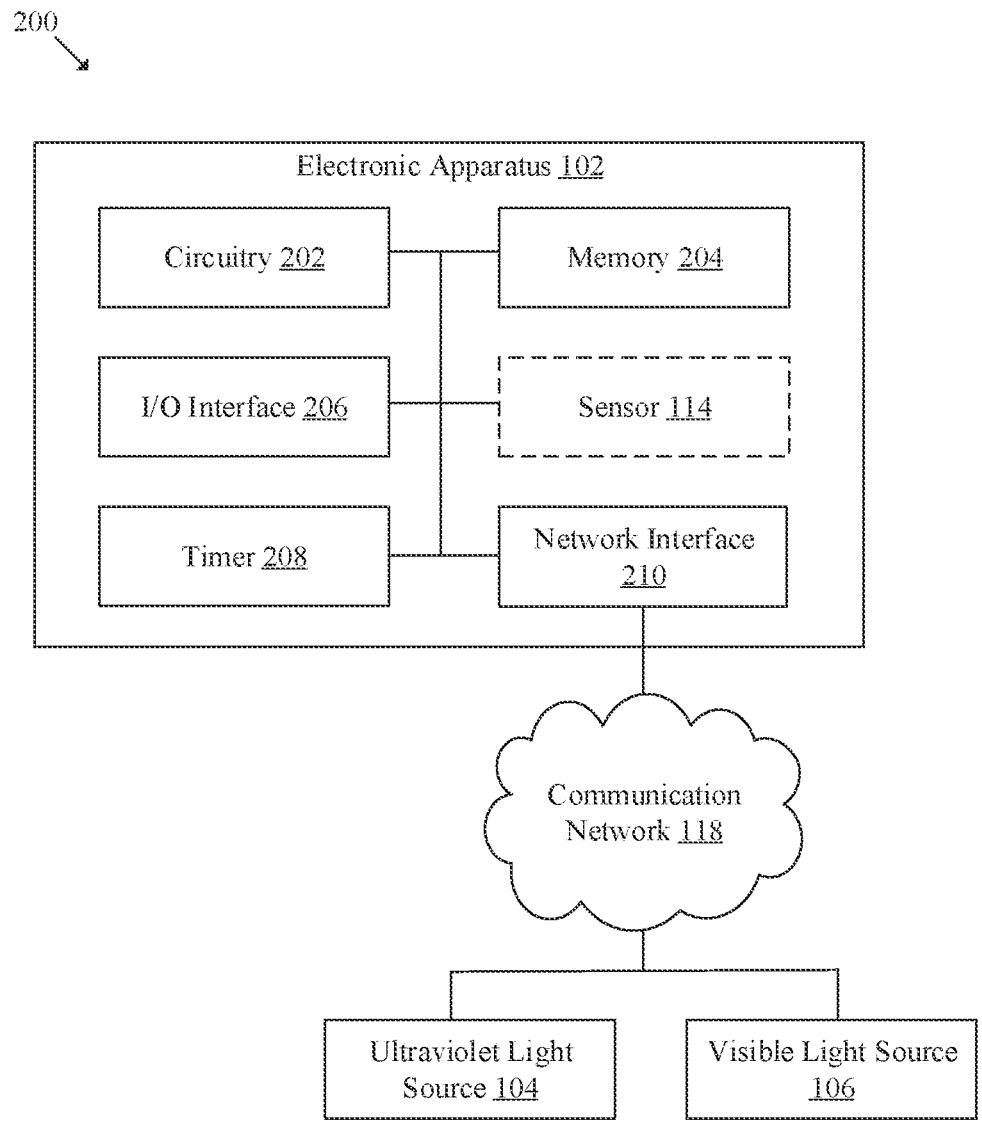
FIG. 2 is a block diagram that illustrates an electronic apparatus to control an ultraviolet light source for disinfection of an object, in accordance with an embodiment of the disclosure.

FIG. 2 is a block diagram that illustrates an electronic apparatus to control an ultraviolet light source for disinfection of an object, in accordance with an embodiment of the disclosure. FIG. 2 is explained in conjunction with elements from FIG. 1. With reference to FIG. 2, there is shown a block diagram 200 of the electronic apparatus 102. The electronic apparatus 102 may include circuitry 202, a memory 204, a I/O interface 206, a timer 208, and a network interface 210. In an embodiment, the electronic apparatus 102 may be communicably coupled to the ultraviolet light source 104 and/or the visible light source 106, via the communication network 118. In another embodiment, the electronic apparatus 102 may be integrally coupled to the ultraviolet light source 104 and/or the visible light source 106. In another embodiment, the electronic apparatus 102 may be separate from the ultraviolet light source 104 and/or the visible light source 106. In another embodiment, the electronic apparatus 102 may be integrally coupled to a user device associated with the second object 112 (such as the user).

The circuitry 202 may include suitable logic, circuitry, and/or interfaces that may be configured to execute program instructions associated with different operations to be executed by the electronic apparatus 102. For example, some of the operations may include, but are not limited to, acquisition of information associated with the first object 108 located in the first physical space 110. The operations may further include, determination, based on the acquired information, one or more control parameters for the ultraviolet light source 104 to disinfect the first object 108. The operations may further include control of the ultraviolet light source 104, based on the determined one or more control parameters, to disinfect the first object 108. The execution of operations by the circuitry 202 may be further described, for example, in FIGS. 3A-3C, 4A, 4B, 5A-5C, 6A-6C, 7A, and 7B.

The circuitry 202 may include any suitable special-purpose or general-purpose computer, computing entity, or processing device including various computer hardware or software modules and may be configured to execute instructions stored on any applicable computer-readable storage media (for example the memory 204). The circuitry 202 may be implemented based on several processor technologies known in the art. For example, the circuitry 202 may include a microprocessor, a microcontroller, a digital signal processor (DSP), an application-specific integrated circuit (ASIC), a Field-Programmable Gate Array (FPGA), or any other digital or analog circuitry configured to interpret and/or to execute program instructions and/or to process data. The circuitry 202 may include any number of processors configured to, individually or collectively, perform any number of operations of the electronic apparatus 102, as described in the present disclosure. Examples of the circuitry 202 may include a Central Processing Unit (CPU), a Graphical Processing Unit (GPU), an x86-based processor, an x64-based processor, a Reduced Instruction Set Computing (RISC) processor, a Complex Instruction Set Computing (CISC) processor, and/or other hardware processors. In an embodiment, the circuitry 202 may control the ultraviolet light source 104 to emit ultraviolet light of a specific wavelength for a specific time period (based on the amount of time) to disinfect the first object 108, based on the determined one or more control parameters (such as the amount of time).

The memory 204 may include suitable logic, circuitry, interfaces, and/or code that may be configured to store the set of instructions executable by the circuitry 202. In an embodiment, the memory 204 may be configured to store information associated with the first object 108 located in the first physical space 110. The stored information may be related to at least one of the location of the first object 108 in the first physical space 110, the distance between the first object 108 and the ultraviolet light source 104, the angular orientation of the first object 108 from the ultraviolet light source 104, or the refractive index of the first object 108. The memory 204 may also store the information about the one or more control parameters related to at least one of the amount of time for emission of an ultraviolet light from the ultraviolet light source 104, the wavelength of the emitted ultraviolet light, or the inclination of the emitted ultraviolet light from the ultraviolet light source 104. In an embodiment, the memory 204 may further store object identification data (such as reference images of objects) associated with different types of objects (such as animate and inanimate objects) in the first physical space 110. In another embodiment, the memory 204 may also store information associated with a level of priority of objects in the first physical space 110.

In an embodiment, the memory may further store information associated with a charging schedule and/or an operational schedule for at least one of the ultraviolet light source 104, the visible light source 106, the sensor 114, and the motorized mechanism 116. The charging schedule or the operational schedule may correspond to a usage pattern (for example, a time-in period and a time-out period of the second object 112) of the first physical space 110 by the second object 112. Based on the stored charging schedule or the operational schedule, the electronic apparatus 102 may switch between the ultraviolet light source 104 and the visible light source 106. In an embodiment, based on the stored charging schedule or the operational schedule, the electronic apparatus 102 may control a plurality of ultraviolet light sources and a plurality of visible light sources, that may be disposed in the first physical space 110. Examples of implementation of the memory 204 may include, but are not limited to, Random Access Memory (RAM), Read Only Memory (ROM), Hard Disk Drive (HDD), a Solid-State Drive (SSD), a CPU cache, and/or a Secure Digital (SD) card.

The I/O interface 206 may include suitable logic, circuitry, interfaces, and/or code that may be configured to receive user input (such as the one or more parameters for the ultraviolet light source 104) from the second object 112 (such as the user) and may render output in response to the received user input from the second object 112. In an embodiment, the I/O interface 206 may be driven by an application installed on the electronic apparatus 102. In some embodiments, the I/O interface 206 may include various input and output devices that may be configured to communicate with the circuitry 202. Examples of the various input and output devices may include, but are not limited to, a touch screen, a keyboard, a mouse, a joystick, a microphone, a display device, a speaker, and/or an image sensor.

The timer 208 may include suitable logic, circuitry, interfaces, and/or code that may be configured to set a countdown timer to start and stop the lighting device 104A associated with the ultraviolet light source 104. In an embodiment, the electronic apparatus 102 may be configured to emit the pulsed illumination from the lighting device 104A for a predefined time period set by the timer 208, from the detection of the second object 112. In an example, the timer 208 may include a digital counter or clock to countdown to the time period and may output a signal to the circuitry 202 once the time period has expired. Examples of the timer 208 may include, but is not limited to, a software timer, a digital clock, or an internal clock associated with the electronic apparatus 102. In an embodiment, the electronic apparatus 102 may activate the timer 208 for the refined time period based on the detection of the second object 112 in the first physical space 110.

The network interface 210 may include suitable logic, circuitry, and interfaces that may be configured to facilitate communication between the circuitry 202 and the communication network 118. The circuitry 202 may acquire information associated with the first object 108 or the second object 112 from the sensor 114 via the network interface 210. The circuitry 202 may control the ultraviolet light source 104 or the visible light source 106 via the network interface 210. The circuitry 202 may further receive software updates for the application installed on the electronic apparatus 102 from a cloud server (not shown) via the network interface 210. The circuitry 202 may further receive object identification data (such reference images of objects) associated with different types of objects (such as animate and inanimate objects) from a cloud server (not shown) via the network interface 210. The network interface 210 may be implemented by use of various known technologies to support wired or wireless communication of the electronic apparatus 102 with the communication network 118. The network interface 210 may include, but is not limited to, an antenna, a radio frequency (RF) transceiver, one or more amplifiers, a tuner, one or more oscillators, a digital signal processor, a coder-decoder (CODEC) chipset, a subscriber identity module (SIM) card, or a local buffer circuitry. The network interface 210 may be configured to communicate via wireless communication with networks, such as the Internet, an Intranet or a wireless network, such as a cellular telephone network, a wireless local area network (LAN), and a metropolitan area network (MAN). The wireless communication may be configured to use one or more of a plurality of communication standards, protocols and technologies, such as Global System for Mobile Communications (GSM), Enhanced Data GSM Environment (EDGE), wideband code division multiple access (W-CDMA), Long Term Evolution (LTE), code division multiple access (CDMA), time division multiple access (TDMA), Bluetooth, Wireless Fidelity (Wi-Fi) (such as IEEE 802.11a, IEEE 802.11b, IEEE 802.11g or IEEE 802.11n), voice over Internet Protocol (VoIP), light fidelity (Li-Fi), Worldwide Interoperability for Microwave Access (Wi-MAX), a protocol for email, instant messaging, and a Short Message Service (SMS).

Although, it is shown in FIG. 2 that the electronic apparatus 102 includes the circuitry 202, the memory 204, the I/O interface 206, the timer 208, and the network interface 210; the disclosure may not be limiting and the electronic apparatus 102 may include more or less components to perform the same or other functions of the electronic apparatus 102. The functions or operations executed by the electronic apparatus 102, as described in FIG. 1, may be performed by the circuitry 202. Operations executed by the circuitry 202 are described, for example, in the FIG. 3, and FIGS. 3A-3C.

FIG. 3A is a diagram that illustrates an exemplary scenario for control of an ultraviolet light source, based on a distance between the ultraviolet light source and an object. FIG. 3A is explained in conjunction with elements from FIGS. 1 and 2. With reference to FIG. 3A, there is shown an exemplary scenario 300A for the control of the ultraviolet light source 104. In the exemplary scenario 300A, there is shown a first object 108 that may be disposed on a base 110A at a first distance 302 from the ultraviolet light source 104 in the first physical space 110. In the exemplary scenario 300A, there is further shown a sensor 114 (such as a camera or a LiDAR sensor) configured to acquire information associated with a distance between the ultraviolet light source 104 and the first object 108. In the exemplary scenario 300A, there is further shown a lighting device 104A, a visible light source 106 and a motorized mechanism 116.

In the exemplary scenario 300A, the circuitry 202 may determine a location of the first object 108 in the first physical space 110. For example, the circuitry 202 may determine that the first object 108 is disposed on the base 110A in the first physical space 110. The circuitry 202 may employ image segmentation techniques on an image captured by the sensor 114 (such as the camera) and detect the first object 108 as an inanimate object (such as a non-living entity) based on the object identification data stored in the memory 204 (shown in FIG. 2). The circuitry may determine that the first object 108 is disposed at a first distance 302 from the ultraviolet light source 104. In an embodiment, the sensor 114 may further output a signal to the circuitry 202 indicating the measured first distance 302 between the ultraviolet light source 104 and the first object 108. The circuitry 202 may compare the measured first distance 302 between the ultraviolet light source 104 and the first object 108 with one or more threshold distances, and may determine that the first object 108 may be located proximate to the ultraviolet light source 104. Based on the location of the first object 108 and the measured first distance 302, the circuitry 202 may control the ultraviolet light source 104 to control the emission of the ultraviolet light. For instance, based on the first distance 302 and the acquired information associated with the first object 108, the circuitry 202 may determine the one or more control parameters (such as a first time period T1 for the emission of the ultraviolet light as shown in FIG. 3C, a first intensity for the emission of the ultraviolet light, or a first wavelength for the emission of the ultraviolet light) for the ultraviolet light source 104. In an example, based on the first distance 302 and the determined one or more control parameters, the circuitry 202 may control the ultraviolet light source 104 to emit the ultraviolet light onto the first object 108 at the first intensity for the first time period T1, to disinfect the first object 108. In another example, based on the first distance 302 and the determined one or more control parameters, the circuitry 202 may control the ultraviolet light source 104 to emit the ultraviolet light onto the first object 108 at the first wavelength for the first time period T1, to disinfect the first object 108. In an embodiment, the circuitry 202 may determine the time period T1 based on a directly proportional linear relationship between the first distance 302 and the time period T1. In another embodiment, the circuitry 202 may determine the time period T1 based on one or more distance ranges (such as 0-2 feet, 2-3 feet, 3-4 feet, and so on) corresponding to one or more threshold distances (such as a first threshold of 2 feet, a second threshold of 3 feet, a third threshold of 4 feet, and so on) within the operational range of the ultraviolet light source 104.

FIG. 3B is a diagram that illustrates an exemplary scenario for control of an ultraviolet light source, based on a distance between the ultraviolet light source and an object. FIG. 3B is explained in conjunction with elements from FIGS. 1, 2, and 3A. With reference to FIG. 3B, there is shown an exemplary scenario 300B for the control of the ultraviolet light source 104. In the exemplary scenario 300B, the first object 108 may be disposed at a second distance 304 from the ultraviolet light source 104. In an embodiment, the second distance 304 may be greater than the first distance 302. In an embodiment, the sensor 114 may output a signal to the circuitry 202 indicating the measured second distance 304 between the ultraviolet light source 104 and the first object 108. The circuitry 202 may compare the measured second distance 304 between the ultraviolet light source 104 and the first object 108 with one or more threshold distances, and may determine that the first object 108 may be located distant to the ultraviolet light source 104. Based on the second distance 304, the circuitry 202 may control the ultraviolet light source 104 to control the emission of the ultraviolet light. For instance, based on the second distance 304 and the acquired information associated with the first object 108, the circuitry 202 may determine the one or more control parameters (such as a second time period T2 for the emission of the ultraviolet light as shown in FIG. 3C, a second intensity for the emission of the ultraviolet light or a second wavelength for the emission of the ultraviolet light) for the ultraviolet light source 104.

In an example, based on the second distance 304 and the determined one or more control parameters, the circuitry 202 may control the ultraviolet light source 104 to emit the ultraviolet light onto the first object 108 at the second intensity for the second time period T2, to disinfect the first object 108. In another example, based on the second distance 304 and the determined one or more control parameters, the circuitry 202 may control the ultraviolet light source 104 to emit the ultraviolet light onto the first object 108 at the second wavelength for the second time period T2, to disinfect the first object 108.

FIG. 3C is a diagram that illustrates an exemplary scenario for control of an ultraviolet light source, based on a distance between the ultraviolet light source and an object. FIG. 3C is explained in conjunction with elements from FIGS. 1, 2, 3A, and 3B. Referring to FIG. 3C, there is shown a graph 300C that illustrates the linearly proportional relationship between the time period (e.g. amount of time for the emission of the ultraviolet light) and the distance between the ultraviolet light source 104 and the first object 108. The graph 300C is a plot between the amount of time for the emission of the ultraviolet light along the X-axis and the distance between the first object 108 and the ultraviolet light source 104 along the Y-axis. From the graph 300C, it may be observed that at least one of the second time period T2 for the emission of the ultraviolet light may be greater than the first time period T1 for the emission of the ultraviolet light, or the second intensity may be greater than the first intensity. The difference in the second time period T2 and the first time period may correspond to a difference between the second distance 304 and the first distance 302. The difference in the second intensity and the first intensity may correspond to the difference between the second distance 304 and the first distance 302. In an embodiment, the circuitry 202 may also control the wavelength of the emitted ultraviolet light based on the difference between the second distance 304 and the first distance 302. Therefore, based on an increase in the distance between the ultraviolet light source 104 and the first object 108, the circuitry 202 may be configured to control at least one of the amount of time for the emission of the ultraviolet light, the intensity of the emitted ultraviolet light, or the wavelength of the emitted ultraviolet light from the ultraviolet light source 104. In an embodiment, the one or more control parameters (such as the intensity of the ultraviolet light, the wavelength of the ultraviolet light, or the amount of time for the emission of the ultraviolet) for the ultraviolet light source 104, to disinfect the first object, are directly proportional to the distance (such as the first distance 302 and the second distance 304) between the first object 108 and the ultraviolet light source 104. In another embodiment, the one or more control parameters (such as the intensity of the ultraviolet light or the amount of time for the emission of the ultraviolet) for the ultraviolet light source 104, to disinfect the first object, may not be directly proportional to the distance (such as the first distance 302 and the second distance 304) between the first object 108 and the ultraviolet light source 104, and may vary based on an ultraviolet light transmittance (including absorption, scattering, or reflection) of the medium (such as air, ozone) between the ultraviolet light source 104 and the first object 108.

FIG. 4A is a diagram that illustrates an exemplary scenario for control of an ultraviolet light source, based on an angular orientation of an object from an ultraviolet light source. FIG. 4A is explained in conjunction with elements from FIGS. 1, 2, and 3A-3C. With reference to FIG. 4A, there is shown an exemplary scenario 400A. In the exemplary scenario 400A, there is shown an ultraviolet light source 104. In the exemplary scenario 400A, there is further shown a first object 108 disposed in a plane that may be parallel to a plane 402 of the base 110A in the first physical space 110. In the exemplary scenario 400A, there is further shown a sensor 114 (such as a camera or a LiDAR sensor) configured to acquire information associated with an angular orientation of the first object 108 with respect to the ultraviolet light source 104. In the exemplary scenario 400A, there is further shown a lighting device 104A, a visible light source 106 and a motorized mechanism 116.

With reference to FIG. 4A, the circuitry 202 may receive a signal from the sensor 114 indicating that the plane of the first object 108 may be parallel to the plane 402 of the base 110A. Based on the received signal, the circuitry 202 may determine that the first object 108 has zero angular orientation with respect to the ultraviolet light source 104. The circuitry 202 may control the motorized mechanism 116 to position the ultraviolet light source 104 with zero inclination with respect to the plane 402 of the base 110A. The ultraviolet light source 104 may control the emission of the ultraviolet light onto all portions of the first object 108 for disinfection of the first object 108, with the exception of a surface 108A of the first object 108.

FIG. 4B is a diagram that illustrates an exemplary scenario for control of an ultraviolet light source, based on an angular orientation of an object from an ultraviolet light source. FIG. 4B is explained in conjunction with elements from FIGS. 1, 2, 3A-3C, and 4A. With reference to FIG. 4B, there is shown an exemplary scenario 400B. In the exemplary scenario 400B, there is further shown the first object 108 that may be inclined at a first angle 404 with respect the plane 402 of the base 110A. Based on the angular orientation of the first object 108 with respect to the ultraviolet light source 104, a portion (such as the surface 108A) of the first object 108 may be concealed from a direct line of sight of the ultraviolet light source 104. In order to disinfect the surface 108A of the first object 108, the circuitry 202 may control the motorized mechanism 116 to change the angular orientation of the ultraviolet light source 104 with respect to the plane 402 of the base 110A. The circuitry 202 may cause the ultraviolet light source 104 to be inclined at a second angle 406 in a direction that may be substantially opposite to a direction of the inclination of the first object 108. The inclination of the ultraviolet light source 104 may change the direction of the emission of the ultraviolet light such that a portion of the emitted ultraviolet light may be directly incident on the surface 108A, and a portion of the ultraviolet light reflected from the base 110A may be incident on the surface 108A. Therefore, the inclination of the ultraviolet light source 104 at the second angle 406 may facilitate the emission of the ultraviolet light towards the surface 108A of the first object 108, and effectively disinfect all areas of the first object 108.

In another embodiment, the acquired information associated with the first object 108 may comprise a refractive index of the first object 108. Based on the refractive index of the first object 108, the circuitry 202 may be further configured to control the one or more control parameters for the ultraviolet light source 104 to disinfect the first object 108. For example, the circuitry 202 may be further configured to the ultraviolet light source 104 to irradiate the first object 108 having a higher refractive index (for example, refractive index of 2.4) for a longer period of time compared to the first object 108 having a lower refractive index (for example, refractive index of 1.4). In another example, the circuitry 202 may be further configured to the ultraviolet light source 104 to irradiate the first object 108 having a higher refractive index with a higher intensity of the ultraviolet light compared to the first object 108 having a lower refractive index. For example, the circuitry 202 may be further configured to irradiate the first object 108 made of a glass material for a longer period of time compared to the first object 108 made of a plastic material. It may be noted that the control of one or more control parameters for the ultraviolet light source 104 to disinfect the first object 108 based on the refractive index of the first object 108, is merely an example, and the circuitry 202 may control one or more control parameters for the ultraviolet light source 104 to disinfect the first object 108 based on other properties (such as surface texture of the first object 108, a transparency of the first object 108, a number of parts that constitute the first object 108, a weight of the first object 108, presence of moisture inside the first object 108, and so on) of the first object 108, without departing from scope of the disclosure.

Figure 5A:
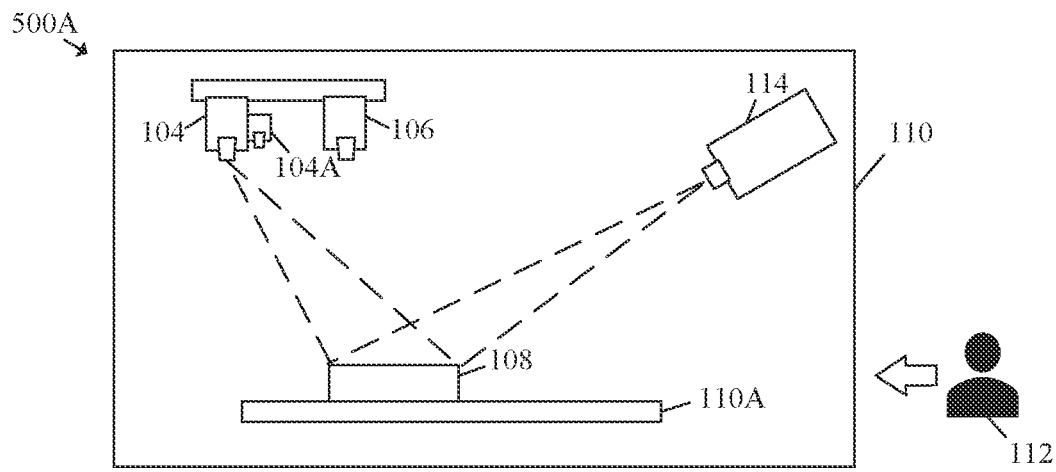
FIGS. 5A-5C are diagrams that collectively illustrate an exemplary scenario for control of an ultraviolet light source for disinfection of a first object, based on detection of a second object, in accordance with an embodiment of the disclosure.

FIG. 5A is a diagram that illustrates an exemplary scenario for control of an ultraviolet light source for disinfection of a first object, based on detection of a second object, in accordance with an embodiment of the disclosure. FIG. 5A is explained in conjunction with elements from FIGS. 1, 2, 3A-3C, 4A, and 4B. With reference to FIG. 5A, there is shown an exemplary scenario 500A. In the exemplary scenario 500A, there is shown an ultraviolet light source 104 configured to irradiate the first object 108 with ultraviolet light. In the exemplary scenario 500A, there is further shown a first object 108 that may be disposed on the base 110A in the first physical space 110. In the exemplary scenario 500A, there is further shown a sensor 114 (such as a camera or an IR sensor) configured to acquire information associated with the first object 108 and a second object 112 within the first physical space 110. In the exemplary scenario 500A, there is further shown a lighting device 104A and a visible light source 106.

In the exemplary scenario 500A, the circuitry 202 may control the ultraviolet light source 104 to irradiate the ultraviolet light onto the first object 108. The circuitry 202 may control the irradiation of the ultraviolet light based on the one or more control parameters (such as the amount of time of the emitted ultraviolet light, the intensity of the emitted ultraviolet light, the wavelength of the emitted ultraviolet light, or the inclination of the emitted ultraviolet light). The one or more control parameters may be determined based on the information (such as the location of the first object 108, the distance of the first object 108 from the ultraviolet light source 104, or the inclination of the first object 108 with respect to the base 110A) acquired from the sensor 114. Based on the irradiation of the ultraviolet light source 104 on the first object 108, the first object 108 may be disinfected. During the disinfection of the first object 108, the sensor 114 may be configured to detect presence or absence of the second object 112 in the first physical space 110. For example, the second object 112 may enter the first physical space 110 from a second physical space (such as an adjacent room or a lobby). Based on the detection of the absence of the second object 112 in the first physical space 110, the ultraviolet light source 104 may continue the irradiation of the ultraviolet light for the disinfection of the first object 108, as described in FIG. 5A. Based on the detection of the presence of the second object in the first physical space 110, the lighting device 104A may be configured to notify the second object 112 about the ongoing disinfection of the first object 108, as described in FIG. 5B.

Figure 5B:
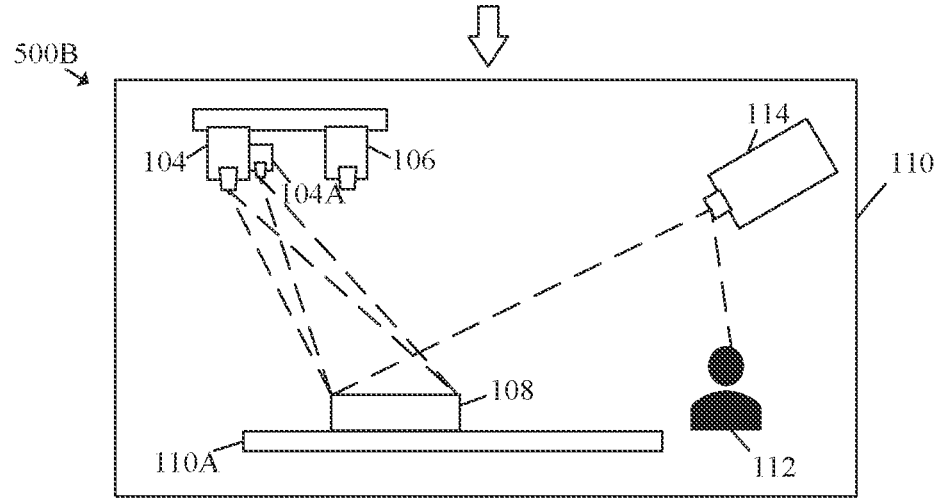

FIG. 5B is a diagram that illustrates an exemplary scenario for control of an ultraviolet light source for disinfection of a first object, based on detection of a second object, in accordance with an embodiment of the disclosure. FIG. 5B is explained in conjunction with elements from FIGS. 1, 2, 3A-3C, 4A, 4B, and 5A. With reference to FIG. 5B, there is shown an exemplary scenario 500B. In the exemplary scenario 500B, the circuitry 202 may receive a signal from the sensor 114 (such as a camera, an IR sensor, or an event camera) in response to detection of the second object 112 (such as an animate object) in the first physical space 110. For example, the first object 108 may be a non-living entity (such as a book, a chair, and the like), and the second object 112 may be a living entity (for example, a human, an animal, and the like). In an example, the sensor 114 (such as a camera) may detect the presence of the second object 112 within the first physical space 110 based on a movement of the second object 112. The circuitry 202 may employ image segmentation techniques on an image captured by the sensor 114 (such as the camera) and detect the second object 112 as a living entity based on the object identification data stored in the memory 204 (shown in FIG. 2). The circuitry 202 may further detect movement of the second object 112 based on object tracking across one or more consecutive images captured by the sensor 114 (such as the camera). In another example, the sensor 114 (such as an IR sensor) may detect the presence of the second object 112 within the first physical space 110 based on a change in infrared radiation within the first physical space 110 due to the presence of the second object 112. Based on the detected presence of the second object 112, the circuitry 202 may control the lighting device 104A to notify the second object 112 about the disinfection of the first object 108 for a first time period. The first time period may correspond to the amount of time (for the emission of the ultraviolet light by the ultraviolet light source 104) that remains subsequent to the detection of the second object 112.

In an embodiment, the notification may include the pulsed illumination of the lighting device 104A that may be associated with the ultraviolet light source 104. In an embodiment, the notification may include the pulsed illumination of a lighting device (no shown) that may be associated with the electronic apparatus 102. The pulsed illumination of the lighting device 104A may include ON and OFF control of the lighting device 104A, or may include alternative illumination by a first color light and a second color light. In another embodiment, the notification may include at least one of an audible alert (such as an alarm or a synthesized speech out from the I/O interface 206 of the electronic apparatus 102) for the second object 112. In another embodiment, the notification may include a vibratory alert for the second object 112. The vibratory alert may include a vibration of an electronic device (such as a mobile phone) associated with the second object 112 (such as a user). In another embodiment, the notification may include at least one of a textual notification (such as a text message), or a graphical notification (such as a popup icon), which may be transmitted to the electronic device (such as the mobile phone) associated with the second object 112 (such as the user). In an example, the lighting device 104A may be configured to project one more characters or symbols (such as a UV radiation warning sign) on to the first object 108 to notify the second object 112 about the disinfection of the first object 108. Thus, the electronic apparatus 102 may ensure safety of the second object 112 (such as the user) by notification of harmful ultraviolet radiation.

Figure 5C:
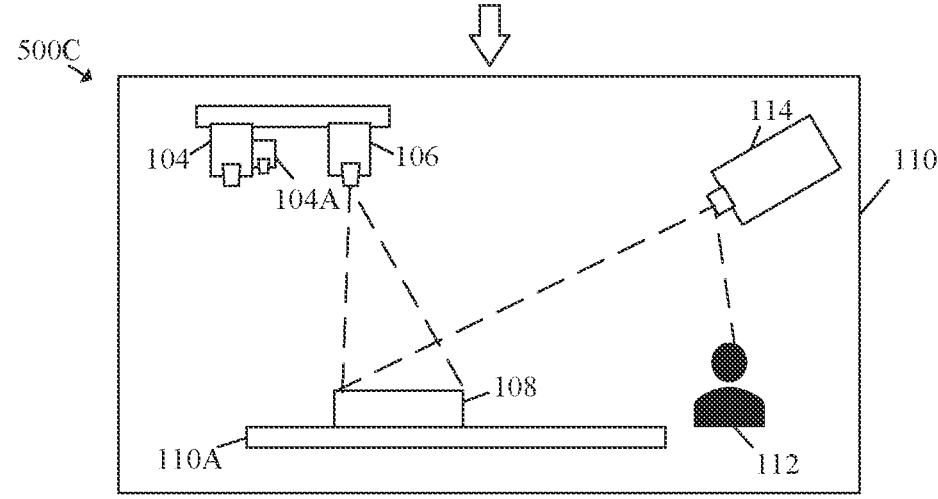

FIG. 5C is a diagram that illustrates an exemplary scenario for control of an ultraviolet light source for disinfection of a first object, based on detection of a second object, in accordance with an embodiment of the disclosure. FIG. 5C is explained in conjunction with elements from FIGS. 1, 2, 3A-3C, 4A, 4B, 5A, and 5B. With reference to FIG. 5C, there is shown an exemplary scenario 500C. In the exemplary scenario 500C, based on the completion of the first time period of the notification by the lighting device 104A, the circuitry 202 may control the visible light source 106 to illuminate the first object 108. In an embodiment, the circuitry 202 may control the ultraviolet light source 104 to switch off based on the detection of the second object 112 in the first physical space 110. In another embodiment, the circuitry 202 may control the ultraviolet light source 104 to switch off based on the completion of the emission of the ultraviolet light for a determined amount of time, or based on the completion of the first time period. Based on the completion of the first time period, the circuitry 202 may be configured to control the visible light source 106 to illuminate the disinfected first object 108 in the first physical space 110.

In another embodiment, based on ultraviolet light source 104 being switched off, the circuitry 202 may switch on the visible light source 106, without any intermittent notification from the lighting device 104A. For example, the circuitry 202 may control the ultraviolet light source 104 to switch off upon completion of the amount of time. Based on the switch off of the ultraviolet light source 104, the circuitry 202 may subsequently control the visible light source 106 to illuminate the disinfected first object 108 in the first physical space 110.

Figure 6A:
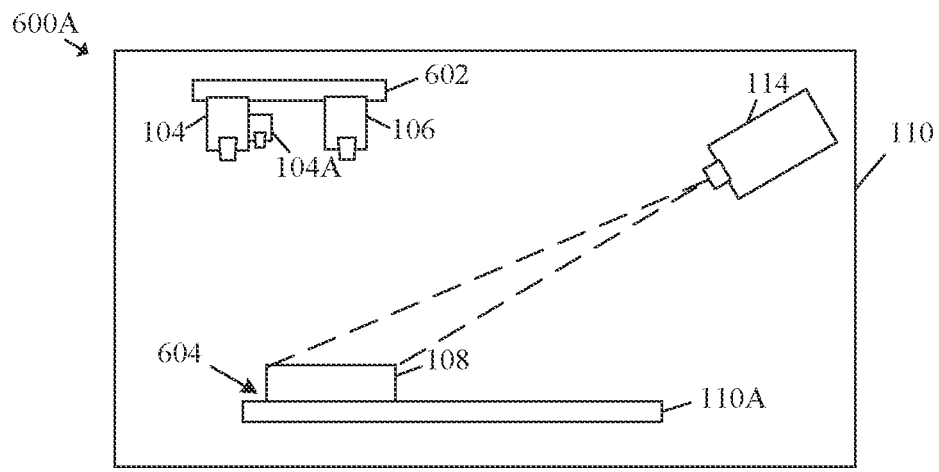
FIGS. 6A-6C are diagrams that collectively illustrate an exemplary scenario for control of an ultraviolet light source, based on detection of a first object as an animate object, in accordance with an embodiment of the disclosure.

FIG. 6A is a diagram that illustrates an exemplary scenario for control of an ultraviolet light source, based on detection of a first object as an animate object, in accordance with an embodiment of the disclosure. FIG. 6A is explained in conjunction with elements from FIGS. 1, 2, 3A-3C, 4A, 4B, and 5A-5C. With reference to FIG. 6A, there is shown an exemplary scenario 600A. With reference to FIG. 6A, there is shown an exemplary scenario 600A. In the exemplary scenario 600A, there is shown an ultraviolet light source 104 configured to irradiate the first object 108 with ultraviolet light. In the exemplary scenario 600A, there is further shown a first object 108 that may be disposed on the base 110A in the first physical space 110. In the exemplary scenario 600A, there is further shown a sensor 114 (such as a camera or an IR sensor) configured to acquire information associated with the first object 108 within the first physical space 110. In the exemplary scenario 600A, there is further shown a lighting device 104A and a visible light source 106.

In an embodiment, the ultraviolet light source 104 may be formed as a first bulb and the visible light source 106 may be formed as a second bulb. In an embodiment, the first bulb and the second bulb may be held by a dual fixture 602. The dual fixture 602 may have a suitable shape, structure or design that may be configured to hold the ultraviolet light source 104 and the visible light source 106. The dual fixture 602 may hold a plurality of ultraviolet light sources and a plurality of visible light sources. In the exemplary scenario 600A, the first object 108 may be disposed at a first position 604 in the first physical space 110. In an embodiment, when the electronic apparatus 102 is switched ON, the circuitry 202 may control the sensor 114 (such as the camera) to detect the first object 108 at the first position 604 in the first physical space 110. The circuitry 202 may control the sensor 114 (such as the camera) to detect movement of the first object 108, as described in FIG. 6B. In another embodiment, in case the sensor 114 (such as the camera) has not detected any movement for a specific period of time (such as 1-3 seconds), the circuitry 202 may perform object detection to classify the first object 108 as one of an animate object or an inanimate object based on the object identification data stored in the memory 204 (shown in FIG. 2). In case the circuitry 202 may determine that the first object 108 is an inanimate object with a threshold level of certainty (such as 99% certainty, the circuitry 202 may control the ultraviolet light source 104 to irradiate the first object 108 with ultraviolet light. In case the circuitry 202 may not determine that the first object 108 is an inanimate object with a threshold level of certainty (for example, 99% certainty), the circuitry 202 may control the sensor 114 (such as an IR sensor) to detect whether the first object 108 emits infrared radiation. The circuitry 202 may control the sensor 114 (such as an IR sensor) to detect whether there exists a difference in infrared radiation between the first object 108 and the surroundings of the first object 108 (such as the base 110A). In another embodiment, the circuitry 202 may employ both the camera and the IR sensor in conjunction to detect whether the first object 108 is an animate object or an inanimate object. Based on the detection, the circuitry 202 may classify the first object 108 as an animate object or an inanimate object, and may accordingly control the ultraviolet light source 104.

Figure 6B:
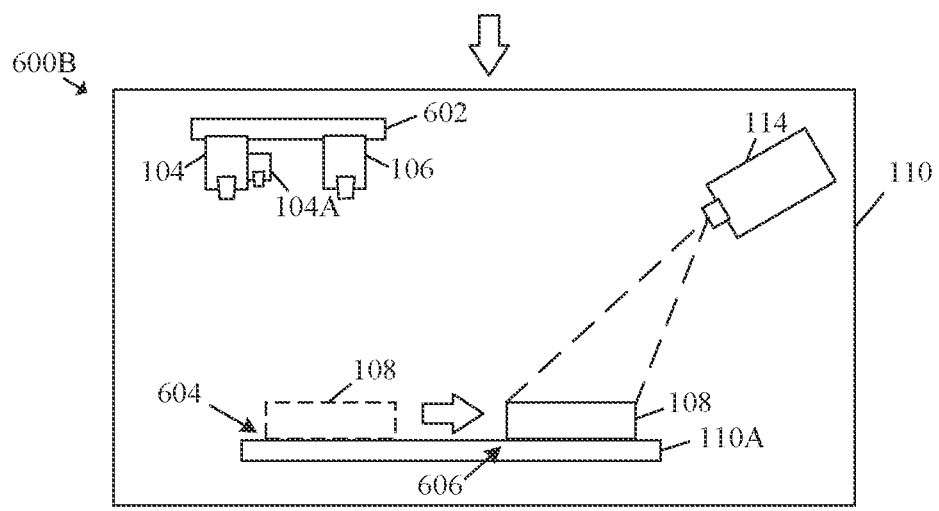

FIG. 6B is a diagram that illustrates an exemplary scenario for control of an ultraviolet light source, based on detection of a first object as an animate object, in accordance with an embodiment of the disclosure. FIG. 6B is explained in conjunction with elements from FIGS. 1, 2, 3A-3C, 4A, 4B, 5A-5C, and 6A. With reference to FIG. 6B, there is shown an exemplary scenario 600B. In the exemplary scenario 600B, the circuitry 202 may receive a signal from the sensor 114 in response to detection of a movement of the first object 108, and may determine that the first object 108 is an animate object (such as a living entity). In case the ultraviolet light source 104 is switched ON, the circuitry 202 may further control the ultraviolet light source 104 to switch OFF based on the detection of the first object 108 as the animate object (such as a living entity). In case the ultraviolet light source 104 is switched OFF, the circuitry 202 may further control the ultraviolet light source 104 to remain switched OFF based on the detection of the first object 108 as the animate object (such as the living entity). In the exemplary scenario 600B, the first object 108 may move from the first position 604 to a second position 606. It may be noted that the exemplary scenario 600A and exemplary scenario 600B may occur as a sequence of events, and the transition from the exemplary scenario 600A (such as the detection of the first object 108) to the exemplary scenario 600B (such as the switching OFF of the ultraviolet light source 104) may occur within a few milliseconds to a few seconds.

Figure 6C:
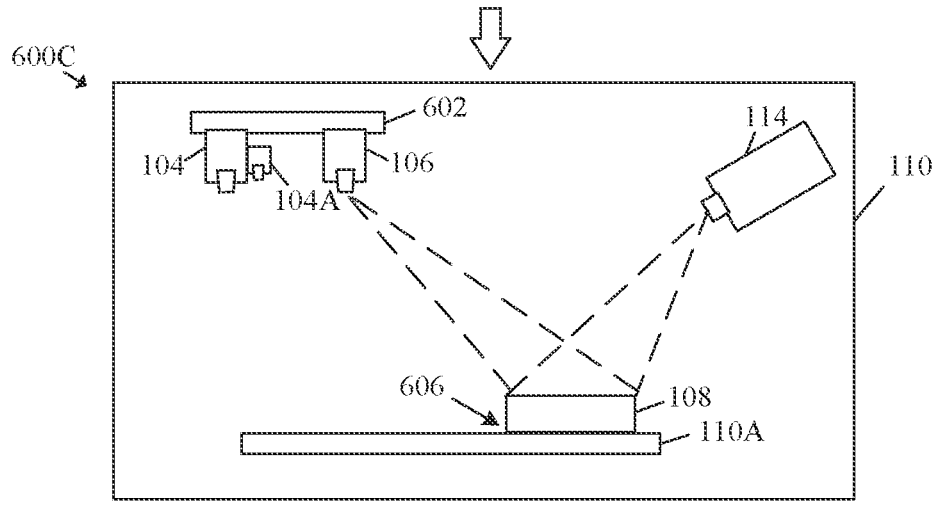

FIG. 6C is a diagram that illustrates an exemplary scenario for control of an ultraviolet light source, based on detection of a first object as an animate object, in accordance with an embodiment of the disclosure. FIG. 6C is explained in conjunction with elements from FIGS. 1, 2, 3A-3C, 4A, 4B, 5A-5C, 6A, and 6B. With reference to FIG. 6C, there is shown an exemplary scenario 600C. In the exemplary scenario 600C, based on the detected movement of the first object 108 from the first position 604 to the second position 606, the circuitry 202 may control the ultraviolet light source 104 to switch OFF, and further control the visible light source 106 to illuminate the first object 108 that may be detected as the animate object (such as the living entity) in the first physical space 110. It may be noted that the exemplary scenario 600A, exemplary scenario 600B, and exemplary scenario 600C may occur as a sequence of events, and the transition from the exemplary scenario 600A (such as the detection of the first object 108) to the exemplary scenario 600C (such as the illumination of the first object 108 by the visible light source 106) may occur within a few milliseconds to a few seconds.

FIG. 7A is a diagram that illustrates an exemplary scenario for control of an ultraviolet light source, based on priority of disinfection, in accordance with an embodiment of the disclosure. FIG. 7A is explained in conjunction with elements from FIGS. 1, 2, 3A-3C, 4A, 4B, 5A-5C, and 6A-6C. With reference to FIG. 7A, there is shown an exemplary scenario 700A. In the exemplary scenario 700A, there is shown an ultraviolet light source 104 configured to emit ultraviolet light. In the exemplary scenario 700A, there is further shown a first object 704, a second object 706, and a third object 708 in the first physical space 110. In the exemplary scenario 700A, there is further shown a sensor 114 (such as a camera, an IR sensor, an audio sensor) configured to acquire information associated with the first object 704, the second object 706, the third object 708, and a user 710 within the first physical space 110. In the exemplary scenario 700A, there is further shown a lighting device 104A and a visible light source 106.

In the exemplary scenario 700A, the ultraviolet light source 104 and the visible light source 106 may be disposed in a single bulb 702. Such configuration of the ultraviolet light source 104 and the visible light source 106 in the single bulb 702 may be compatible for assembly with existing bulb fixtures, and thereby improve convenience and reduce cost. Further, in the exemplary scenario 700A, there may be a user 710 in the first physical space 110, who may enter the first physical space 110 and access at least one of the first object 704 (such as a door knob), the second object 706 (such as a chair), or the third object 708 (such as a floor mat). Based on actions of the user 710, the circuitry 202 may control the sensor 114 to acquire information associated with a set of objects (such as the first object 704, the second object 706, or the third object 708) including the first object 108 in the first physical space 110. The acquired information may indicate positional and orientational information of the set of objects (such as the first object 704, the second object 706, or the third object 708) including the first object 108 in the first physical space 110, and information regarding the interaction of the user 710 with the set of objects (such as the first object 704, the second object 706, or the third object 708). As shown in FIG. 1A, the user 710 may use the first object 704 (such as a door knob) to exit the first physical space 110.

FIG. 7B is a diagram that illustrates an exemplary scenario for control of an ultraviolet light source, based on priority of disinfection, in accordance with an embodiment of the disclosure. FIG. 7B is explained in conjunction with elements from FIGS. 1, 2, 3A-3C, 4A, 4B, 5A-5C, 6A-6C, and 7A. With reference to FIG. 7B, there is shown an exemplary scenario 700B. In the exemplary scenario 700B, the circuitry 202 may determine a type of each object of the set of objects (such as, the first object 704, the second object 706, or the third object 708) based on the acquired information in the first physical space 110. For instance, information associated with the type of object may be categorized as a frequently accessed object, or an infrequently accessed object from the set of objects. In one example, the first object 704 may be categorized as the frequently accessed object, and the other objects (such as, the second object 706, and the third object 708) from the set of objects as infrequently accessed objects.

The circuitry 202 may further determine the one or more control parameters (such as the amount of time, the intensity, the wavelength, or the inclination of the emitted ultraviolet light) for disinfection of each object based on the determined type (such as, the frequently accessed object or the infrequently accessed object). The circuitry 202 may further control the ultraviolet light source 104 to disinfect each object (such as, the first object 704, the second object 706, or the third object 708) based on the determined one or more control parameters for each object in the first physical space 110. For example, in case the object is categorized as the frequently accessed object (such as the first object 704), the circuitry 202 may control the ultraviolet light source 104 to irradiate the first object 704 with the ultraviolet light of higher intensity compared to the ultraviolet light used to irradiate the infrequently accessed object (such as the second object 706 or the third object 708). In an embodiment, the ultraviolet light emitted by the ultraviolet light source 104 may be a focused spot-beam, as shown in FIG. 7B. The focused spot-beam from the ultraviolet light source 104 may target a specific area of the first object 704 (such as the door knob) with high intensity ultraviolet light. For example, the ultraviolet light source 104 may be configured to irradiate a portion of the first object 704, which may have come in tactile contact with the user 710, via the focused spot-beam.

In another embodiment, the information associated with the type of object may be related to a material of each object (such as, the first object 704, the second object 706, or the third object 708) from the set of objects. The circuitry 202 may be configured to determine the one or more control parameters to control the ultraviolet light source 104, based on the material of the object in the first physical space 110. In yet another embodiment, the circuitry 202 may be configured to determine a level of priority for disinfection of each object (such as, the first object 704, the second object 706, and the third object 708) of the set of objects based on the determined type of each object in the first physical space 110. For example, the first object 704 (such as the door knob of a door for a hospital room) may be a high touch surface compared to the second object 706 (such as the chair), or the third object 708 (such as the floor mat). Therefore, the circuitry 202 may assign a higher priority to the first object 704 for disinfection. The circuitry 202 may accumulate such information related to high tough surfaces among objects in the first physical space 110 based on past events or based on user input, and may determine the level of priority for disinfection. Based on the determined level of priority, the circuitry 202 may control the ultraviolet light source 104 to irradiate each object (such as, the first object 704, the second object 706, and the third object 708) of the set of objects in the first physical space 110 in an order based on the determined level of priority for disinfection of each object (for example, disinfect the first object 704 prior to disinfection of the second object 706 and the third object 708). In another embodiment, the circuitry 202 may be configured to control the emission of the ultraviolet light to irradiate the first object 704 based on detection of usage (such as contact of the first object 704 with the user 710) of the first object 704 by the sensor 114, to thereby timely disinfect the first object 704 post usage and prior to subsequent use of the first object 704. The circuitry 202 may control the ultraviolet light source 104 to irradiate the first object 704 with the ultraviolet light based on the detection that user is no longer in contact with the first object 704, or the user has moved away from the first object 704.

Figure 8:
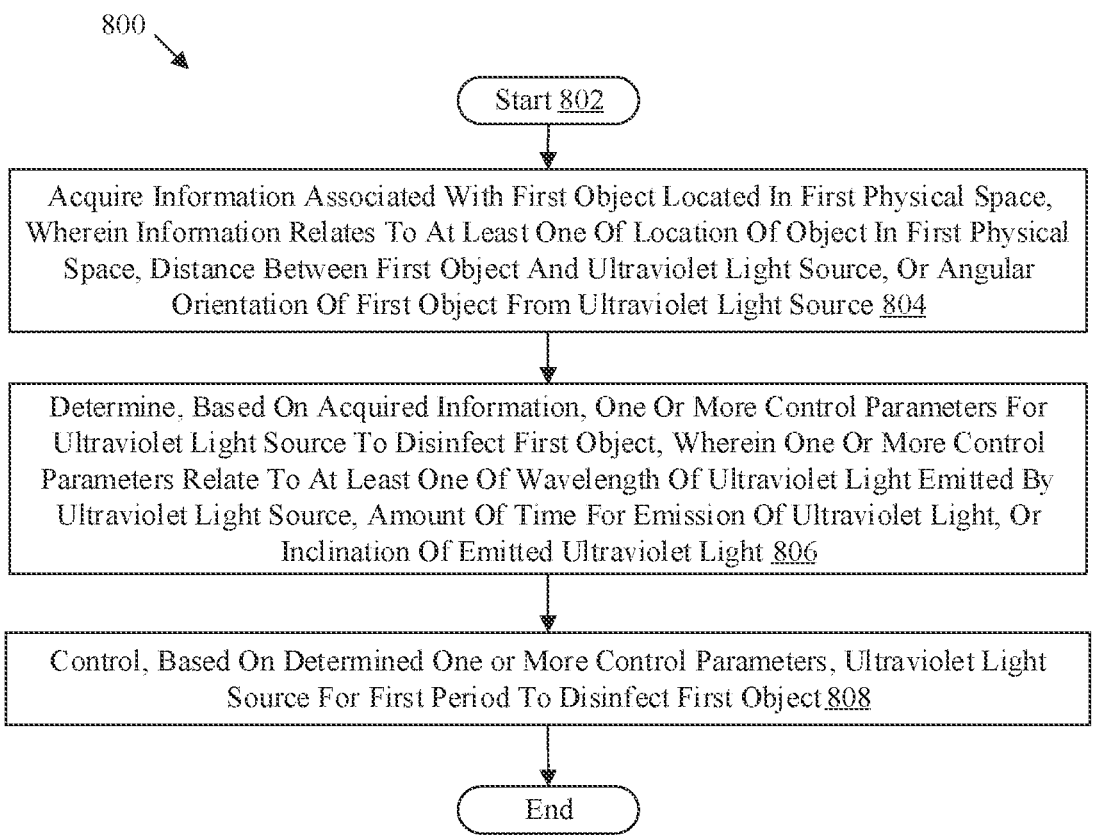
FIG. 8 is a flowchart that illustrates exemplary operations for control of an ultraviolet light source coupled with the electronic apparatus of FIG. 1 for disinfection of an object, in accordance with an embodiment of the disclosure.

FIG. 8 is a flowchart that illustrates exemplary operations for control of an ultraviolet light source coupled with the electronic apparatus of FIG. 1 for disinfection of an object, in accordance with an embodiment of the disclosure. FIG. 8 is explained in conjunction with elements from FIGS. 1, 2, 3A-3C, 4A, 4B, 5A-5C, 6A-6C, 7A, and 7B. With reference to FIG. 8, there is shown a flowchart 800. The method illustrated in the flowchart 800 may start from 802.

At 802, the information associated with a first object (such as the first object 108) located in a first physical space (such as the first physical space 110) may be acquired. The information may be related to at least one of the location of the first object 108 in the first physical space 110, the distance between the first object 108 and an ultraviolet light source (such as the ultraviolet light source 104), or the angular orientation of the first object 108 from the ultraviolet light source 104. In an embodiment, the electronic apparatus 102 may be configured to acquire information associated with the first object 108 located in the first physical space 110, as described in FIGS. 1, 2, 3A-3C. 4A, and 4B.

At 804, the one or more control parameters for the ultraviolet light source 104 to disinfect the first object 108 may be determined. The one or more control parameters may be related to at least one of the amount of time for emission of the ultraviolet light from the ultraviolet light source 104, the wavelength of the emitted ultraviolet light, or the inclination of the emitted ultraviolet light. In an embodiment, the electronic apparatus 102 may be configured to determine the one or more control parameters for the ultraviolet light source 104 to disinfect the first object 108, as described in FIGS. 1, 2, 3A-3C, 4A, and 4B.

At 806, the ultraviolet light source 104 may be controlled to disinfect the first object 108, based on the determined one or more control parameters. In an embodiment, the electronic apparatus 102 may control the ultraviolet light source 104 to disinfect the first object, based on the determined one or more control parameters. Control may pass to end.

The flowchart 800 is illustrated as discrete operations, such as 802, 804, and 806. However, in certain embodiments, such discrete operations may be further divided into additional operations, combined into fewer operations, or eliminated, or rearranged depending on the implementation without detracting from the essence of the disclosed embodiments.

Various embodiments of the disclosure may provide a non-transitory computer-readable medium and/or storage medium, and/or a non-transitory machine readable medium and/or storage medium stored thereon, a set of instructions executable by a machine and/or a computer (for example the electronic apparatus 102) for the control of the ultraviolet light source 104 for disinfection of an object. The set of instructions may be executable by the machine and/or the computer (for example the electronic apparatus 102) to perform operations that may include acquisition of information associated with a first object (such as the first object 108) located in a first physical space (such as the first physical space 110). The information may be related to at least one of the location of the first object 108 in the first physical space 110, the distance between the first object 108 and an ultraviolet light source (such as the ultraviolet light source 104), or the angular orientation of the first object 108 from the ultraviolet light source 104. The operations may further include a determination, based on the acquired information, of one or more control parameters for the ultraviolet light source 104 to disinfect the first object 108. The one or more control parameters may be related to at least one of the amount of time for emission of the ultraviolet light from the ultraviolet light source 104, the wavelength of the emitted ultraviolet light, or the inclination of the emitted ultraviolet light. The operations may further include control, based on the determined one or more control parameters, of the ultraviolet light source 104 to disinfect the first object 108.

Exemplary aspects of the disclosure may include an electronic apparatus (such as, the electronic apparatus 102) that may include circuitry (such as, the circuitry 202). The circuitry 202 may be configured to acquire information associated with a first object (such as the first object 108) located in a first physical space (such as the first physical space 110). The information may be related to at least one of the location of the first object 108 in the first physical space 110, the distance between the first object 108 and an ultraviolet light source (such as the ultraviolet light source 104), or the angular orientation of the first object 108 from the ultraviolet light source 104. The circuitry 202 may be configured to determine, based on the acquired information, one or more control parameters for the ultraviolet light source 104 to disinfect the first object 108. The one or more control parameters may be related to at least one of the amount of time for emission of the ultraviolet light from the ultraviolet light source 104, the wavelength of the emitted ultraviolet light, or the inclination of the emitted ultraviolet light. The circuitry 202 may be configured to control, based on the determined one or more control parameters, the ultraviolet light source 104 to disinfect the first object 108.

In accordance with an embodiment, the circuitry 202 may be further configured to control an intensity of the ultraviolet light source 104 based on the distance the between the first object 108 and the ultraviolet light source 104. The circuitry 202 may be configured to control the ultraviolet light source 104 to emit the ultraviolet light at the controlled intensity for the amount of time. The circuitry 202 may be further configured to control the ultraviolet light source 104 to switch off upon completion of the amount of time. The circuitry 202 may be further configured to control a visible light source (such as the visible light source 106) to illuminate the disinfected first object in the first physical space 110.

In accordance with an embodiment, the ultraviolet light source 104 may be a first bulb and the visible light source 106 may be a second bulb. The first bulb and the second bulb may be held by a dual fixture. In accordance with an embodiment, the ultraviolet light source 104 and the visible light source 106 may be disposed in a single bulb.

In accordance with an embodiment, the circuitry 202 may be further configured to control the ultraviolet light source 104 to switch off based on a detection of an animate object as the first object 108. The circuitry 202 may be further configured to control the visible light source 106 to illuminate the first object 108 detected as the animate object in the first physical space 110.

In accordance with an embodiment, the circuitry 202 may be further configured to detect a second object (such as the second object 112), as an animate object, in the first physical space 110. The circuitry 202 may be further configured to notify the second object 112 about the disinfection of the first object 108. The notification may comprise at least one of a pulsed illumination of a lighting device (such as the lighting device 104A) associated with the electronic apparatus 102 or with the ultraviolet light source 104, or an audible alert for the second object 112.

In accordance with an embodiment, the circuitry 202 may be further configured to control the ultraviolet light source 104 to switch off based on the detection of the second object 112 in the first physical space 110. The circuitry 202 may be further configured to control the visible light source 106 to illuminate the disinfected first object 108 for the second object 112 in the first physical space 110. The disinfected first object 108 may be different from the second object 112.

In accordance with an embodiment, the circuitry 202 may be communicably coupled with at least one sensor (such as the sensor 114) to acquire the information associated with the second object 112 in the first physical space 110. The circuitry 202 may be further configured to control the sensor 114 to detect the first object 108 in the first physical space 110. The circuitry 202 may be further configured to determine the information associated with the second object 112 based on the detected first object 108 within the first physical space 110.

In accordance with an embodiment, the acquired information indicates a set of objects (such as the first object 704, the second object 706, or the third object 708) including the first object 704 in the first physical space 110. The circuitry 202 may be further configured to determine a type of each object in the set of objects based on the acquired information in the first physical space 110. The circuitry 202 may be further configured to determine the one or more control parameters for each object based on the determined type. The circuitry 202 may be further configured to control the ultraviolet light source 104 to disinfect each object of the set of objects based on the determined one or more control parameters for each object in the first physical space 110.

In accordance with an embodiment, the circuitry 202 may be further configured to determine a level of priority for disinfection for each object of the set of objects (such as the first object 704, the second object 706, or the third object 708) based on the determined type of each object in the first physical space 110. The circuitry 202 may be further configured to control the ultraviolet light source 104 to disinfect each object in the set of objects based on the determined level of priority for disinfection for each object in the first physical space 110.

In accordance with an embodiment, the ultraviolet light emitted by the ultraviolet light source 104 may be a focused spot-beam. In accordance with an embodiment, the one or more control parameters related to at least one of an intensity of the ultraviolet light, the wavelength of the ultraviolet light, or the amount of time for the emission of the ultraviolet light, may be directly proportional to the information associated with the distance between the first object 108 and the ultraviolet light source 104.

In accordance with an embodiment, the acquired information associated with the first object 108 may comprise a refractive index of the first object 108. Based on the refractive index of the first object 108, the circuitry 202 may be further configured to control the one or more control parameters for the ultraviolet light source 104 to disinfect the first object 108.

In accordance with an embodiment, the ultraviolet light source 104 may positioned on a motorized mechanism (such as the motorized mechanism 116). The circuitry 202 may be further configured to control the motorized mechanism 116 to further control the inclination of the ultraviolet light source 104, based on the acquired information as the angular orientation of the first object 108 in the first physical space 110.

The foregoing description of embodiments and examples has been presented for purposes of illustration and description. It is not intended to be exhaustive or limiting to the forms described. Numerous modifications are possible considering the above teachings. Some of those modifications have been discussed and others will be understood by those skilled in the art. The embodiments were chosen and described for illustration of various embodiments. The scope is not limited to the examples or embodiments set forth herein but can be employed in any number of applications and equivalent devices by those of ordinary skill in the art. Rather it is hereby intended the scope be defined by the claims appended hereto. Additionally, the features of various implementing embodiments may be combined to form further embodiments.

For the purposes of the present disclosure, expressions such as "including", "comprising", "incorporating", "consisting of", "have", "is" used to describe and claim the present disclosure are intended to be construed in a non-exclusive manner, namely allowing for items, components or elements not explicitly described also to be present. Reference to the singular is also to be construed to relate to the plural. Further, all joinder references (e.g., attached, affixed, coupled, connected, and the like) are only used to aid the reader's understanding of the present disclosure, and may not create limitations, particularly as to the position, orientation, or use of the systems and/or methods disclosed herein. Therefore, joinder references, if any, are to be construed broadly. Moreover, such joinder references do not necessarily infer that two elements are directly connected to each other.

The present disclosure may be realized in hardware, or a combination of hardware and software. The present disclosure may be realized in a centralized fashion, in at least one computer system, or in a distributed fashion, where different elements may be spread across several interconnected computer systems. A computer system or other apparatus adapted for carrying out the methods described herein may be suited. A combination of hardware and software may be a general-purpose computer system with a computer program that, when loaded and executed, may control the computer system such that it carries out the methods described herein. The present disclosure may be realized in hardware that includes a portion of an integrated circuit that also performs other functions. It may be understood that, depending on the embodiment, some of the steps described above may be eliminated, while other additional steps may be added, and the sequence of steps may be changed.

The present disclosure may also be embedded in a computer program product, which includes all the features that enable the implementation of the methods described herein, and which when loaded in a computer system is able to carry out these methods. Computer program, in the present context, means any expression, in any language, code or notation, of a set of instructions intended to cause a system with an information processing capability to perform a particular function either directly, or after either or both of the following: a) conversion to another language, code or notation; b) reproduction in a different material form.

While the present disclosure has been described with reference to certain embodiments, it will be understood by those skilled in the art that various changes may be made, and equivalents may be substituted without departing from the scope of the present disclosure. In addition, many modifications may be made to adapt a situation or material to the teachings of the present disclosure without departing from its scope. Therefore, it is intended that the present disclosure is not limited to the embodiment disclosed, but that the present disclosure will include all embodiments that fall within the scope of the appended claims.

What is claimed is:

1. An electronic apparatus, comprising:
    circuitry communicably coupled with an ultraviolet light source, wherein
        the ultraviolet light source is on a motorized mechanism, and
        the circuitry is configured to:
            acquire information associated with a first object located in a first physical space, wherein the information relates to at least one of: a location of the first object in the first physical space, a distance between the first object and the ultraviolet light source, or an angular orientation of the first object with respect to the ultraviolet light source;
            determine, based on the acquired information, one or more control parameters for the ultraviolet light source to disinfect the first object, wherein the one or more control parameters relate to at least one of: an amount of time for emission of an ultraviolet light by the ultraviolet light source, a wavelength of the emitted ultraviolet light, or an inclination of the ultraviolet light source;
            control, based on the determined one or more control parameters, the ultraviolet light source to disinfect the first object; and
            control the motorized mechanism to change the inclination of the ultraviolet light source, wherein the control of the motorized mechanism is based on the acquired information related to the angular orientation of the first object with respect to the ultraviolet light source.

2. The electronic apparatus according to claim 1, wherein
    the circuitry is further communicably coupled with a visible light source, and
    the circuitry is further configured to:
        control an intensity of the ultraviolet light source based on the distance between the first object and the ultraviolet light source;
        control the ultraviolet light source to emit the ultraviolet light at the controlled intensity for the amount of time;
        control the ultraviolet light source to switch off upon completion of the amount of time; and
        control the visible light source to illuminate the disinfected first object in the first physical space.

3. The electronic apparatus according to claim 2, wherein
    the ultraviolet light source is a first bulb,
    the visible light source is a second bulb, and
    the first bulb and the second bulb are held by a dual fixture.

4. The electronic apparatus according to claim 2, wherein the ultraviolet light source and the visible light source are in a single bulb.

5. The electronic apparatus according to claim 2, wherein the circuitry is further configured to:
   control the ultraviolet light source to switch off based on a detection of an animate object as the first object; and
   control the visible light source to illuminate the first object detected as the animate object in the first physical space.

6. The electronic apparatus according to claim 1, wherein the circuitry is further configured to:
   detect a second object, as an animate object, in the first physical space, wherein the second object accesses the first physical space from a second physical space; and
   notify the second object about the disinfection of the first object, wherein the notification comprises at least one of: a pulsed illumination of a lighting device associated with the electronic apparatus or with the ultraviolet light source, or an audible alert for the second object.

7. The electronic apparatus according to claim 6, wherein the circuitry is further configured to:
   control the ultraviolet light source to switch off based on the detection of the second object in the first physical space; and
   control a visible light source, that is communicably coupled with the circuitry, to illuminate the disinfected first object for the second object in the first physical space, wherein the disinfected first object is different from the second object.

8. The electronic apparatus according to claim 1, wherein
   the circuitry is communicably coupled with at least one sensor to acquire the information associated with a second object in the first physical space, and
   the circuitry is further configured to:
      control the at least one sensor to detect the first object in the first physical space; and
      determine the information associated with the second object based on the detected first object within the first physical space.

9. The electronic apparatus according to claim 1, wherein the acquired information further indicates a set of objects including the first object in the first physical space, and the circuitry is further configured to:
   determine a type of each object in the set of objects based on the acquired information in the first physical space;
   determine the one or more control parameters for each object based on the determined type; and
   control the ultraviolet light source to disinfect each object in the set of objects based on the determined one or more control parameters for each object in the first physical space.

10. The electronic apparatus according to claim 9, wherein the circuitry is further configured to:
   determine a level of priority of disinfection for each object in the set of objects based on the determined type of each object in the first physical space; and
   control the ultraviolet light source to disinfect each object in the set of objects based on the determined level of priority of the disinfection for each object in the first physical space.

11. The electronic apparatus according to claim 1, wherein the ultraviolet light emitted by the ultraviolet light source is a focused spot-beam.

12. The electronic apparatus according to claim 1, wherein the one or more control parameters that relate to at least one of: an intensity of the ultraviolet light, the wavelength of the ultraviolet light, or the amount of time for the emission of the ultraviolet light, are directly proportional to the information associated with the distance between the first object and the ultraviolet light source.

13. The electronic apparatus according to claim 1, wherein
   the acquired information associated with the first object further comprises a refractive index of the first object, and
   based on the refractive index of the first object, the circuitry is further configured to control the one or more control parameters for the ultraviolet light source to disinfect the first object.

14. An electronic apparatus, comprising:
   circuitry communicably coupled with an ultraviolet light source, wherein the circuitry is configured to:
      acquire information associated with a first object located in a first physical space, wherein the information relates to at least one of: a location of the first object in the first physical space, a distance between the first object and the ultraviolet light source, or an angular orientation of the first object with respect to the ultraviolet light source;
      determine, based on the acquired information, one or more control parameters for the ultraviolet light source to disinfect the first object, wherein the one or more control parameters relate to at least one of: an amount of time for emission of an ultraviolet light by the ultraviolet light source, a wavelength of the emitted ultraviolet light, or an inclination of the emitted ultraviolet light;
      control, based on the determined one or more control parameters, the ultraviolet light source to disinfect the first object;
      detect a second object, as an animate object, in the first physical space, wherein the second object accesses the first physical space from a second physical space; and
      notify the second object about the disinfection of the first object, wherein the notification comprises at least one of: a pulsed illumination of a lighting device associated with the electronic apparatus or with the ultraviolet light source, or an audible alert for the second object.

* * * * *